(12) United States Patent
Zakrewsky et al.

(10) Patent No.: US 10,449,254 B2
(45) Date of Patent: Oct. 22, 2019

(54) IONIC LIQUIDS FOR TRANSDERMAL DRUG DELIVERY

(71) Applicants: The Regents of the University of California, Oakland, CA (US); Triad National Security, LLC, Los Alamos, NM (US); The Arizona Board of Regents c/o Northern Arizona University, Flagstaff, AZ (US)

(72) Inventors: Michael Zakrewsky, Santa Barbara, CA (US); Samir Mitragotri, Santa Barbara, CA (US); David T. Fox, Los Alamos, NM (US); Andrew Koppisch, Flagstaff, AZ (US); Rico Del Sesto, Irvins, UT (US); Katherine Lovejoy, Silver Spring, MD (US)

(73) Assignees: The Regents of the University of California, Oakland, CA (US); Triad National Security, LLC, Los Alamos, NM (US); Arizona Board of Regents c/o Northern Arizona University, Flagstaff, AZ (US)

( * ) Notice: Subject to any disclaimer, the term of this patent is extended or adjusted under 35 U.S.C. 154(b) by 43 days.

(21) Appl. No.: 15/034,138

(22) PCT Filed: Nov. 3, 2014

(86) PCT No.: PCT/US2014/063745
§ 371 (c)(1),
(2) Date: May 3, 2016

(87) PCT Pub. No.: WO2015/066647
PCT Pub. Date: May 7, 2015

(65) Prior Publication Data
US 2016/0263225 A1 Sep. 15, 2016

Related U.S. Application Data

(60) Provisional application No. 61/899,294, filed on Nov. 3, 2013.

(51) Int. Cl.
| | | |
|---|---|---|
| *A01N 43/00* | (2006.01) | |
| *A01N 43/46* | (2006.01) | |
| *A61K 31/55* | (2006.01) | |
| *A61K 47/24* | (2006.01) | |
| *A61K 9/00* | (2006.01) | |
| *A61K 47/12* | (2006.01) | |
| *A01N 33/12* | (2006.01) | |
| *A01N 43/36* | (2006.01) | |
| *A61K 31/047* | (2006.01) | |
| *A61K 31/545* | (2006.01) | |
| *A61K 31/66* | (2006.01) | |
| *A61K 47/18* | (2017.01) | |

(52) U.S. Cl.
CPC ............. *A61K 47/24* (2013.01); *A01N 33/12* (2013.01); *A01N 43/36* (2013.01); *A61K 9/0014* (2013.01); *A61K 31/047* (2013.01); *A61K 31/545* (2013.01); *A61K 31/66* (2013.01); *A61K 47/12* (2013.01); *A61K 47/186* (2013.01)

(58) Field of Classification Search
None
See application file for complete search history.

(56) References Cited

U.S. PATENT DOCUMENTS

| | | | | |
|---|---|---|---|---|
| 4,892,737 A | * | 1/1990 | Bodor | A61K 47/12 424/449 |
| 5,965,610 A | * | 10/1999 | Modak | A01N 25/32 424/401 |
| 6,858,217 B2 | * | 2/2005 | Kerschner | A61K 8/31 424/400 |
| 7,102,000 B2 | * | 9/2006 | Pfahl | C07D 277/20 544/137 |

(Continued)

FOREIGN PATENT DOCUMENTS

| | | | | |
|---|---|---|---|---|
| CA | 2471414 C | * | 11/2011 | ........... A61K 8/0237 |
| JP | 2008184407 | | 4/2008 | |

(Continued)

OTHER PUBLICATIONS

Abbott et al. (Eutectic-Based Ionic Liquids with Metal-Containing Anions and Cations Chem.—Eur. J. Jul., 27 2007, 13, 6495-6501.*

(Continued)

*Primary Examiner* — Layla Soroush
(74) *Attorney, Agent, or Firm* — Pabst Patent Group LLP

(57) ABSTRACT

The compositions and methods described herein are topically applied to the skin with negligible or no skin irritation and can direct or prevent transport through the skin. The compositions contain neat ionic liquids, optionally in combination with a drug to be delivered. In a preferred embodiment, the compositions increase transdermal transport of the drug to be delivered. In some embodiments, the compositions disrupt bacterial biofilms. This is particularly beneficial in the treatment of antibiotic resistant skin infections. In other embodiments, the compositions direct delivery within the skin. In still other embodiments, the compositions prevent transfer of substances through the stratum corneum. The disclosed compositions and methods can be tuned and modified such that they can be used to treat or prevent a variety of different diseases and disorders.

7 Claims, 11 Drawing Sheets

(56) References Cited

U.S. PATENT DOCUMENTS

| | | | |
|---|---|---|---|
| 2010/0256174 A1 | 10/2010 | Yamaguchi |
| 2014/0322307 A1 | 10/2014 | Ferrer |
| 2015/0342852 A1 | 12/2015 | Van Den Nest |

FOREIGN PATENT DOCUMENTS

| | | |
|---|---|---|
| JP | 2008184402 | 8/2008 |
| WO | 2007124397 | 11/2007 |
| WO | 2008031105 | 3/2008 |
| WO | 2009066457 | 5/2009 |
| WO | 2011056545 | 5/2011 |

OTHER PUBLICATIONS

Abbott, et al., "Design of improved eutectic solvents using hole theory", ChemPhysChem, 7(4): p. 803-806.
Abbott, et al., "Novel solvent properties of choline chloride/urea mixtures", Chem. Commun. (Camb), (1): 70-71 (2003).
Baker, et al., "Fluorescence studies of protein thermostability in ionic liquids", Chemical Commun (Camb), (8): 940-1 (2004).
Brown, et al. "Dermal and transdermal drug delivery systems: current and future prospects", Drug Delivery, 13:175-87 (2006).
Carson, et al., "Antibiofilm activities of 1-alkyl-3-methylimidazolium chloride ionic liquids", Green Chem,, 11(4):492-7 (2009).
Del Sesto, et al., "Tetraalkylphosphonium-based ionic liquids", J Organometallic Chem., 690(10): 2536-42 (2005).
Dobler, et al., "Ionic liquids as ingredients in topical drug delivery", Int J Pharma, 441((1-2):620-7 (2013).
Hayyan, et al., "Glucose-based deep eutectic solvents: Physical properties", J Mol Liq., 178: 137-41 (2013).
Hough, et al., "The third evolution of ionic liquids: active pharmaceutical ingredients", New J Chem., 31:1429-36 (2007).
International Search Report for corresponding PCT application PCT/US2014/063745 dated Apr. 28, 2015.
Karande, et al., "Design principles of chemical penetration enhancers for transdermal drug delivery", PNAS, 102:4688-93 (2005).
Karande, et al., "Discovery of transdermal penetration enhancers by high-throughput screening", Nat Biotechnol, 22(2):192-7 (2004).
Lovejoy, et al., "Utilization of Metal Halide Species Ambiguity to Develop Amorphous, Stabilized Pharmaceutical Agents As Ionic Liquids"Crystal Growth & Design, 12(11): p. 5357-5364 (2012).
MacFarlane, et al., "Pyrrolidinium imides: A new family of molten salts and conductive plastic crystal phases,"J Phys Chem., 103(20):4164-70 (1999).
Martin, et al., "Impact of physicochemical properties of engineered fullerenes on key biological responses", Toxicol Appl Pharmacol., 234(1):58-67 (2009).
Palmer, et al., "Molecular techniques to detect biofilm bacteria in long bone nonunion: a case report", Clin orthop relat Res., 469:3037-42 (2011).
Wilkes, et al., "Dialkylimidazolium Chloroalurninate Melts—a New Class of Room-Temperature Ionic Liquids for Electrochemistry, Spectroscopy and Synthesis", Inorg Chem., 21(3):1263-64 (1982).
Yu, et al., "Biodegradable naphthenic acid ionic liquids: synthesis, characterization, and quantitative structure-biodegradation relationship", Chem., 14(35):11174-82 (2008).
Am. Chem., "Efficacy of ionic liquids for pathogen neutralization: Turntable solvents as anti-biofilm agents" Abstracts, 39th Northeast Regional meeting of the American Chemical Society, New Haven, Ct., Oct. 23-26, 1 page, Oct. 25, 2013.
Partial European Search Report dated May 29, 2017, in European Patent Application No. 14859243.9.

\* cited by examiner

IONIC LIQUIDS FOR TRANSDERMAL DRUG DELIVERY

CROSS-REFERENCE TO RELATED APPLICATION

This application is a 371 application of International Application No. PCT/US2014/063745, filed Nov. 3, 2014, which claims priority to provisional application, U.S. Application No. 61/899,294, filed Nov. 3, 2013, the disclosure of which is incorporated herein by reference in its entirety.

FIELD OF THE INVENTION

The field of the invention is transdermal drug delivery formulations, and topically administered formulations, such as for the treatment of infections, and methods for making and using these formulations and devices.

BACKGROUND OF THE INVENTION

Topical and transdermal drug delivery provide many advantages over other common delivery routes like oral, subcutaneous, and intravenous. These advantages include avoidance of major degradative pathways associated with the GI tract, reduction in side effects associated with systemic toxicity, and needle-free drug administration. Brown, et al., "*Dermal and transdermal drug delivery systems: current and future prospects*", Drug Delivery, 13:175-87 (2006). Unfortunately, the outermost layer of the skin, the stratum corneum (SC), functions as a barrier to most foreign material and severely limits passive diffusion of many molecules. To overcome this barrier, several strategies have been employed including the use of chemical penetration enhancers (CPEs). CPEs have been shown to enhance transport through the skin, for a variety of molecules, by disrupting the lipid composition and organization in the SC. Karande, et al., "*Design principles of chemical penetration enhancers for transdermal drug delivery*", Proceedings of the National Academy of Sciences of the United States of America, 102:4688-93 (2005). However, the extent of lipid disruption often correlates closely with skin irritation. Karande 2005. Therefore, a balance between transport enhancement and skin irritation is often required before a CPE-based drug formulation can be commercialized.

Concurrently, for the treatment of bacterial skin infections, a second transport barrier to drug delivery exists—the bacterial biofilm. Biofilm-protected bacteria account for 65% of bacterial infections in humans and are 50-500 times more resistant to antibiotics than unprotected bacteria. Palmer, et al., "*Molecular techniques to detect biofilm bacteria in long bone nonunion: a case report*", Clinical orthopaedics and related research, 469:3037-42 (2011). The antibiotic resistance is due to the transport barrier posed by extracellular polymeric substances (EPS), e.g. polysaccharides, humic acids and nucleic acids. Although the chemical composition of the SC and bacterial biofilm are distinctive, overcoming the transport barrier posed by the SC and biofilm can be accomplished in a similar manner, such as through fluidization or extraction of the barrier components by a suitable solvent.

There is a need for compositions and methods that improve transdermal transport, but do not irritate the skin. There is also a need for improved compositions to inhibit microbial growth on biological and synthetic surfaces.

Therefore it is an object of the invention to provide compositions for improving transdermal transport of therapeutic, prophylactic, or diagnostic agents.

It is a further object of the invention to provide improved compositions for the treatment of diseases and disorders within the skin, such as infections.

It is a further object of the invention to provide methods and compositions for inhibiting microbial growth.

It is yet a further object of the invention to provide methods for improving transdermal transport of therapeutic, prophylactic, or diagnostic agents.

It is a still further object of the invention to provide improved methods for treatment of diseases and disorders of the skin.

SUMMARY OF THE INVENTION

The compositions and methods described herein are topically applied to the skin with negligible or no skin irritation (as evidenced by redness, burning and/or itching sensations) and can direct or prevent transport through the skin. The compositions contain neat ionic liquids, optionally in combination with a drug to be delivered. In a preferred embodiment, the compositions enhance skin penetration. These compositions are applied topically to the surface of the skin and increase transdermal transport of the drug to be delivered.

In some embodiments, the compositions disrupt bacterial biofilms. This is particularly beneficial in the treatment of antibiotic resistant skin infections.

In other embodiments, the compositions contain ILs that are able to direct delivery within the skin. In still other embodiments, the compositions are able to prevent transfer of substances through the stratum corneum. Such compositions may be useful as a protective coating on the skin.

The compositions can be tuned and modified such that they can be used to treat or prevent a variety of different diseases and disorders.

BRIEF DESCRIPTION OF THE DRAWINGS

FIG. 2A 0.5 µM 3H-Mannitol was added to each of the ILs (LANL-6, LANL-13, LANL-14, LANL-19, LANL-21) and applied to the porcine skin. FIG. 2B 14.3 µM 3H-Cefadroxil was added the IL (LANL-21) and applied to the porcine skin. Error bars represent mean±s.e. for n=3.

FIG. 4A: Average cfu/mL cell counts for n=6, all data points. Error=standard deviation of n=6. FIG. 4B: Biofilm age comparison—72 hour *pseudomonas* (black bar) and 24 hour *pseudomonas* (open bar); FIG. 4C: Biofilm species comparison—24 hour *pseudomonas* (black bar) and 24 hour *salmonella* (open bar).

FIG. 5A: All data points. FIG. 5B: Biofilm age comparison (72 hours (black bar) versus 24 hours (open bar) for *P. aeruginosa* (*Pseudomonas*)). FIG. 5C: Biofilm species comparison after 24 hours (*S. enterica* (*Salmonella*) open bar, *P. aeruginosa* (*Pseudomonas*) black bar).

DETAILED DESCRIPTION OF THE INVENTION

Figure 1:
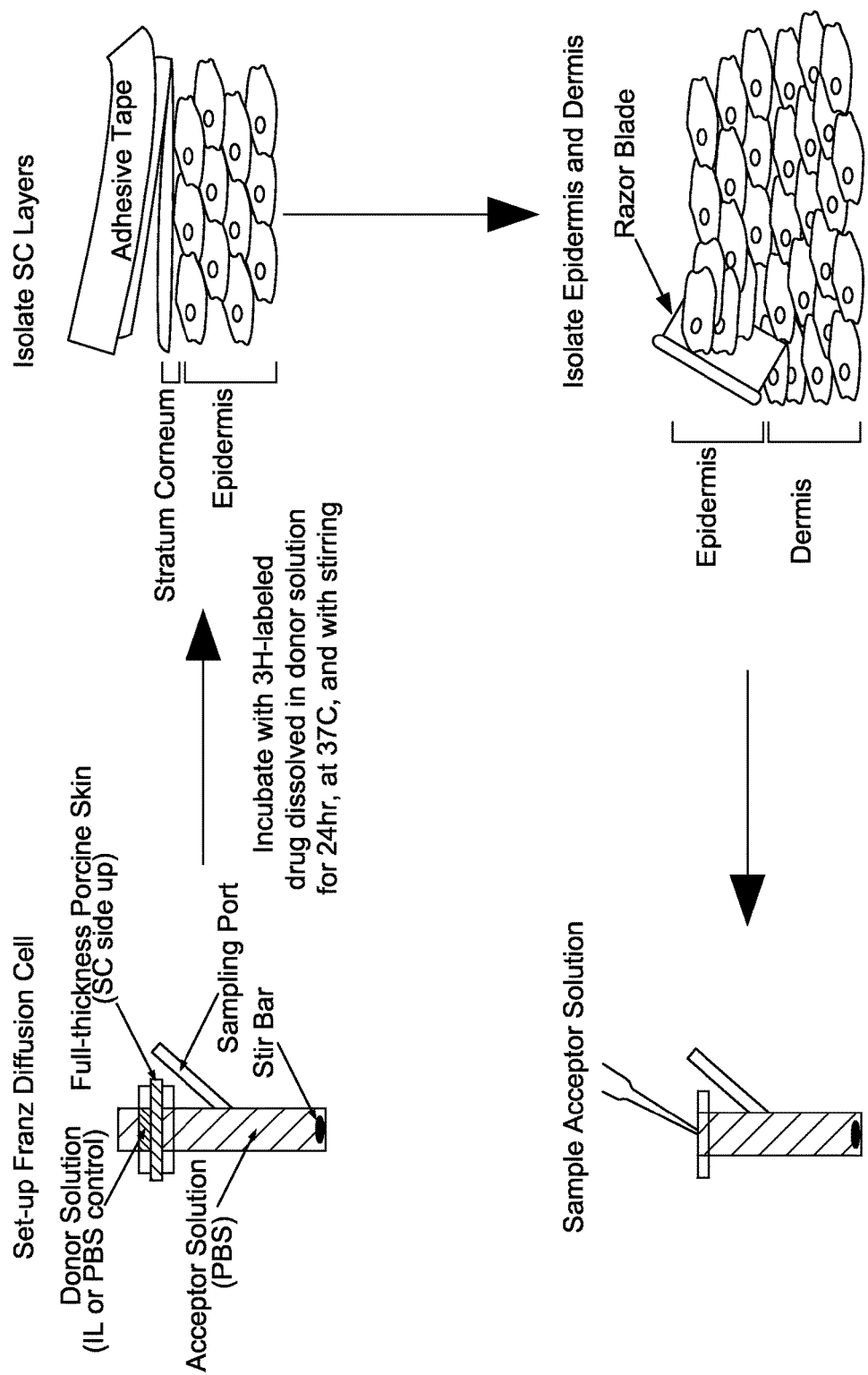
FIG. 1 is a schematic of the skin transport experiment set-up and analysis. Porcine skin was loaded into the Franz diffusion cell (FDC) with the stratum corneum (SC) facing up. Skin was incubated in contact with 3H-labeled drug dissolved in donor solution for 24 hrs, at 37° C., with stirring. After 24 hrs the donor solution was removed and skin thoroughly washed. The SC was separated from the epidermis by tape stripping. Ten tape strips were applied, each tape corresponding to 1 "layer" of SC. Ten tape strips were assumed to remove the entire SC. Epidermis was separated from dermis using a razor blade. Acceptor solution was collected, and drug transport into various tissue layers was quantified by scintillation counter.

The compositions contain neat ionic liquids, which do not form or contain emulsions or microemulsions under standard storage and application conditions (e.g. room temperature and pressure). The ionic liquids typically contain at least one cationic component and at least one anionic component. Preferably at least one of the components of the ionic liquid is a chemical permeation enhancer, preferably both the cationic and anionic components are chemical permeation enhancers. The compositions preferably also contain a drug to be delivered. Optionally, one of the ionic components is also the drug to be delivered.

The compositions are applied topically to an individual's skin in an effective amount to increase transdermal drug delivery. When applied to an individual's skin, the compositions do not cause undue irritation, such as evidenced by redness, burning and/or itching sensations.

In some embodiments, in addition to increasing the rate and/or amount of drug transport through the skin, the compositions disrupt bacterial biofilms. Thus, these compositions may be used to treat bacterial infections, optionally antibiotic resistant skin infections. In these embodiments, the composition optionally, does not include a drug to be delivered, and the composition may contain an effective amount of the ionic liquids to treat the infection.

I. Drug-Containing Compositions for Targeted Drug Delivery

The compositions contain at least two components, which can be at least two ionic components, or at least one ionic component and a drug to be delivered. Preferably the ionic liquid contains two or more, more preferably two ionic components. In some embodiments, the compositions also contain a drug to be delivered transdermally. The compositions may be used to administer a wide range of drugs. In some embodiments, the ILs are effective at removing bacterial biofilm from a skin site. In these embodiments, optionally, the composition does not contain an additional drug to be delivered. In some embodiments, the composition is applied to a synthetic surface, such as the surface of a medical device to inhibit microbial growth.

A. Ionic Liquids

The term "ionic liquids (ILs)" as used herein refers to organic salts or mixtures of organic salts which are in liquid state at room temperature. This class of solvents has been shown to be useful in a variety of fields, including in industrial processing, catalysis, pharmaceuticals, and electrochemistry. The ionic liquids contain at least one anionic and at least one cationic component. Optionally, the IL contains an additional hydrogen bond donor (i.e. any molecule that can provide an —OH or an —NH group), examples include but are not limited to alcohols, fatty acids, and amines.

In some embodiments, the cationic or anionic component is also a drug.

The at least one anionic and at least one cationic component may be present in any molar ratio. Exemplary molar ratios (cation:anion) are provided in Table 2. Exemplary molar ratios (cation:anion) include but are not limited to 1:1, 1:2, 2:1, 1:3, 3:1, 2:3, 3:2, and ranges between these ratios.

The compositions disclosed herein typically contain an ionic liquid. The ability to modulate either the cation or anion individually presents an advantageous framework for tuning secondary and tertiary characteristics without sacrificing the primary function of the IL. Hough, et al., "*The third evolution of ionic liquids: active pharmaceutical ingredients*", New Journal of Chemistry, 31:1429 (2007).

Each of the components in the IL (i.e., anionic and cationic components) or ionic component(s) in the IL and drug may on its own be irritating to the skin. However, the combination of the ionic components (or ionic component and drug) used in the composition is not irritating when applied to the surface of the skin.

Exemplary ionic liquids are described in International Patent Application Publication No. WO 07/124397 to Grinstaff et al. hereby incorporated by reference in its entirety. Exemplary ionic liquids with antimicrobial properties are described in WO 2011/056545 to Grinstaff et al. hereby incorporated by reference in its entirety.

The ionic liquids may include organic cations that contain independently for each occurrence a heterocycle selected from the group consisting of azathiozoles, pyrazoles, thiazoles, isothiazoles, oxothiazoles, oxazines, oxazo lines, oxazoboroles, dithioazoles, triazoles, selenozoles, oxaphopholes, pyrroles, boroles, furans, thiophenes, phospholes, pentazoles, indoles, indolines, oxazoles, isoozazoles, isotriazoles, tetrazoles, benzofurans, dibenzofurans, benzothiophenes, dibenzothiophenes, thiadiazoles, pyrimidines, pyrazines, pyridazines, piperazines, pipidines, morpholenes, pyrans, annolines, phthalzines, quinazolines, quinoxalines, quino lines, isoquinolines, thazines, oxazines, and azaannulenes. The ionic liquids may include acyclic organic cations, such as amines such as amidines, imines, guanidines, phosphines such as phosphinimines, arsines, stibines, ethers, thioethers, and selenoethers.

The ionic liquids may include organic and inorganic anions that contain independently for each occurrence a carboxylic acid, sulfonic acid, tetrafluoroborate, hexafluorophosphate, bis-trifluoromethane-sulfonimide, and derivatives thereof. Additional anionic species that can be included in the ionic liquid include, but are not limited to, fatty acids, alcohols, borates, phosphates, nitrates, sulfates, triflates, antimonates, carboranes, poly-oxo metallates, and metalloboranes.

In some embodiments, the IL is a deep eutectic solvent (DES). A DES is a type of ionic solvent with special properties composed of a mixture which forms a eutectic with a melting point much lower than either of the individual components. Exemplary DES include, but are not limited to, choline oleate, choline hexanoate, choline geranate, choline malonate (choline disodium malonate), and urea-choline. In these the formulation is a DES and not a true ionic liquid because excess carboxylate precludes 1:1 ion pairing.

One or more of the components may be a chemical permeation enhancer.

Preferably the ionic liquid contains $[P(C_{14}H_{29})(C_6H_{13})^3]^+$ ("$PR_4$") in combination with an anionic component, preferably the anionic component is a salt of a fatty acid. Exemplary fatty acids include, but are not limited to, myristoleic acid, palmitoleic acid, sapienic acid, oleic acid, elaidic acid, geranic acid, vaccenic acid, linoleic acid, linoelaidic acid, α-linolenic acid, arachidonic acid, eicosapentaenoic acid, erucic acid, docosahexaenoic acid, propionic acid, butyric acid, valeric acid, hexanoic acid, enanthic acid, caprylic acid, pelargonic acid, capric acid, undecylic acid, lauric acid, tridecyclic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, or hexatriacontylic acid. Preferred fatty acid salts include sodium oleate, sodium geranate, or sodium hexanoate.

Physical Properties for Cationic and Anionic Components of the IL

Preferably, materials that are used as transdermal delivery agents have viscosities below about 1500 cP at room temperature when measured using a standard viscometer, such as Viscolab 3000 viscometer (Cambridge Viscosity, Medford, Mass.).

Figure 6:
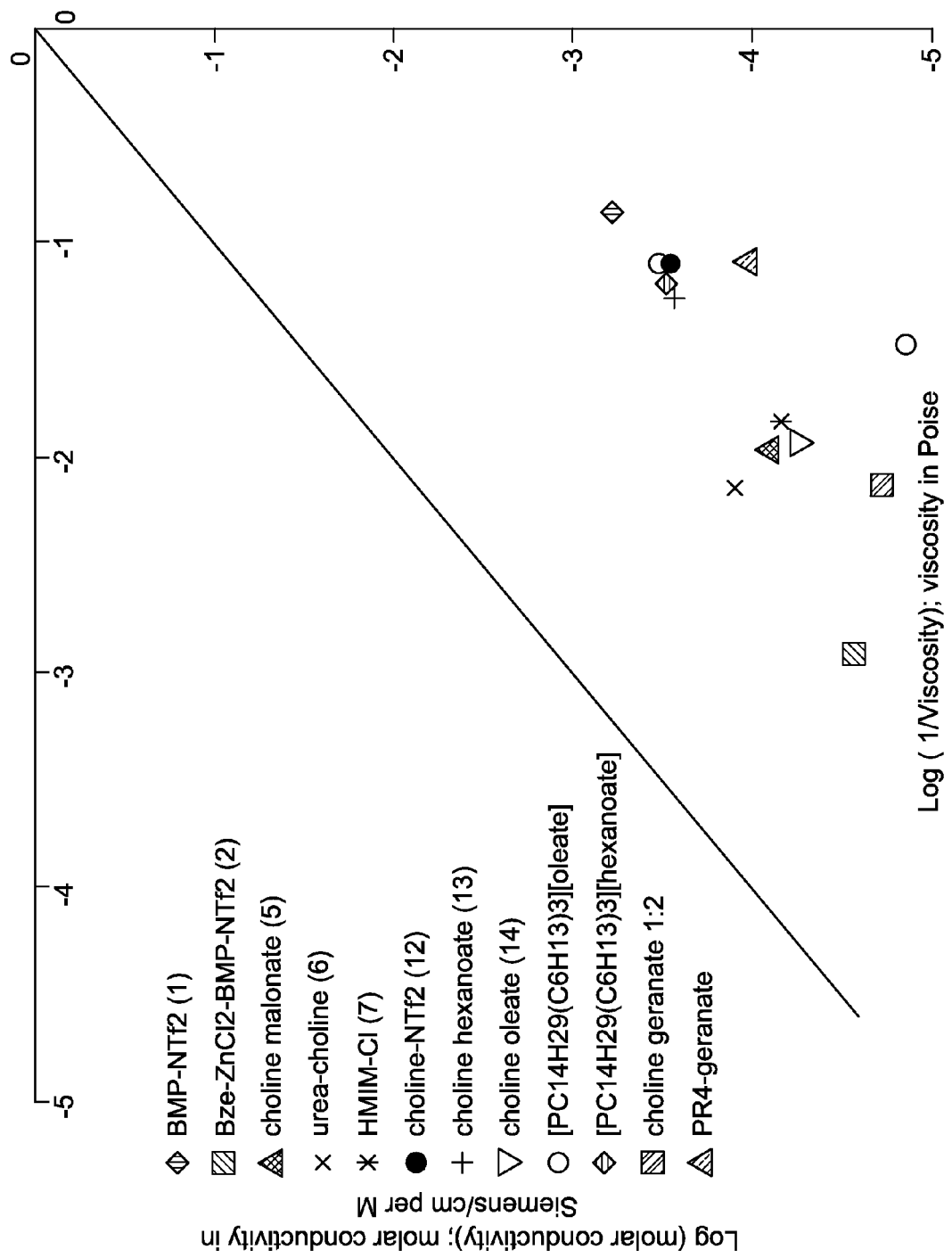
FIG. 6 is a Walden plot of materials tested (Log (molar conductivity) (molar conductivity in S/cm/M) versus Log (1/viscosity) (viscosity in Poise).

The relationship between viscosity and conductance of ionic liquid may provide insight on the mobility of ions in the IL, e.g., are the cations and anions tightly associated as cation-anion pairs or flowing freely. The Walden rule, that the product of molar conductivity and viscosity is a constant value, holds for pure ionic liquids. Xu, et al., "*Ionic Liquids: Ion Mobilities, Glass Temperatures, and Fragilities*", Journal of Physical Chemistry B, 107(25): 6170-6178 (2003). FIG. 6 shows a Walden plot for which an ideal Walden line for a dilute aqueous solution of fully dissociated KCl has slope=1. A low conductivity indicates that the cation-anion pairs are highly associated and would be favorable for transdermal delivery. A low viscosity is also conducive to transport through skin.

In some embodiments, the ionic liquids for transdermal drug formulation have room temperature values in the lower right side of the Walden plot. As shown in the Examples, some of the materials showing the best skin transport properties fall in the lower right portion of the plot, such as PR4-oleate and choline geranate.

The ionic liquids may be selected such that their conductivities and viscosities at room temperature when plotted on a Walden plot are located in the lower right portion of the Walden plot.

Chemical Permeation Enhancers

As used herein "chemical permeation enhancer" or "CPE" generally means a chemical that aids transport across the epithelium of the skin (stratum corneum), such as by altering the structure of the cellular membrane (transcellular route) and/or the tight junctions between cells (paracellular route) of the stratum corneum.

Exemplary cationic CPEs include, but are not limited to cationic surfactants, cationic polymers (e.g., polylysine, polyethylene imine, polyarginine), fatty amines, and nitrogen-containing rings Exemplary anionic CPEs include, but are not limited to, anionic surfactants (e.g., sodium lauryl sulfate, sodium decyl sulfate, sodium octylsulfate), and salts of fatty acids.

Table 1 below list some exemplary CPEs characterized by charge (charge is indicated in parentheses) and category. Some are not charged but may be able to become charged or have charged derivatives. Additional CPEs are known and disclosed in KARNADE 2005, the disclosure of which is incorporated herein by reference.

TABLE 1

CPEs characterized by charge and category

| Abbreviation | Chemical Name | Category | CAS Number |
|---|---|---|---|
| SLS(−) | Sodium lauryl sulfate | AS | 151-21-3 |
| SDS(−) | Sodium decyl sulfate | AS | 142-87-0 |
| SOS(−) | Sodium octyl sulfate | AS | 142-31-4 |
| SLA(−) | Sodium laureth sulfate | AS | 68585-34-2 |
| NLS(−) | N-Lauryl sarcosinate | AS | 137-16-6 |
| CTAB(+) | Cetyltrimethyl ammonium bromide | CS | 57-09-0 |
| DTAB(+) | Decyltrimethyl ammonium bromide | CS | 2082-84-0 |
| BDAC(+) | Benzyldimethyl dodecyl ammonium chloride | CS | 139-07-1 |
| TTAC(+) | Myristyltrimethyl ammonium chloride | CS | 4574-04-3 |
| DPC(+) | Dodecyl pyridinium chloride | CS | 104-74-5 |
| DPS | Decyldimethyl ammonio propane sulfonate | ZS | 15163-36- |
| MPS | Myristyldimethyl ammonio propane sulfonate | ZS | 14933-09-6 |
| PPS | Palmityldimethyl ammonio propane sulfonate | ZS | 2281-11-0 |
| CBC | ChemBetaine CAS | ZS | N/A (mixture) |
| CBO | ChemBetaine Oleyl | ZS | N/A (mixture) |
| PCC | Palmitoyl carnitine chloride | ZS | 6865-14-1 |
| SDC(−) | Sodium deoxycholate | BS | 302-95-4 |
| SGC(−) | Sodium glycocholate | BS | 863-57-0 |
| CA(−) | Cholic acid | FA | 73163-53-8 |
| HA(−) | Hexanoic acid | FA | 142-91-6 |
| HPA(−) | Heptanoic acid | FA | 111-14-8 |
| SOA(−) | Sodium oleate | SS | 143-19-1 |
| UR | Urea | FM | 57-13-6 |
| LAM(+) | Lauryl amine | FM | 124-22-1 |
| CL | Caprolactam | NR | 105-60-2 |
| MP(+) | Methyl pyrrolidone | NR | 872-50-4 |
| OP(+) | Octyl pyrrolidone | NR | 2687-94-7 |
| MPZ(+) | Methyl piperazine | NR | 109-01-3 |
| PPZ(+) | Phenyl piperazine | NR | 92-54-6 |

Targeted Delivery

The compositions may be selected to deliver a drug to a particular site, such as within the stratum corneum, epidermis and/or dermis, or through and beyond all of the layers of the skin. As shown in the examples, different ILs demonstrated three different transport regimes, depending on the IL employed: 1) Drug retention in the donor solution. 2) Enhanced localization and retention within the SC, epidermis, and dermis. 3) Enhanced transdermal penetration through all layers of the skin and into the acceptor solution. In all of the embodiments, the composition is not irritating to the skin, although one or more of the components on its own may be irritating.

In some embodiments, the components of the composition (e.g. cationic component, anionic component, and/or drug) are selected such that the drug to be delivered is delivered within the layers of the skin. This may be particularly useful for the treatment of diseases or disorders of the skin, such as treatment of an infection, cut, burn, or rash.

In other embodiments, the components of the composition (e.g. cationic component, anionic component, and/or drug) are selected such that the drug to be delivered is transported through the skin.

In still other embodiments, the components of the composition may be selected such that they prevent transfer of a drug (or other substance) through the stratum corneum. This may be useful as a coating to protect the skin or treat large open wounds.

B. Drugs to be Delivered

The drug to be delivered transdermally may be any chemical or biological molecules providing a therapeutic, diagnostic, or prophylactic effect in vivo. The drug-containing compositions may contain any suitable drug. The drug is selected based on the disease or disorder to be treated or prevented. The drug can be a small molecule or macromolecule, such as a protein or peptide. In the preferred embodiment the drug is a protein or peptide. However, a wide range of drugs may be included in the compositions. Drugs contemplated for use in the formulations described herein include, but are not limited to, the following categories and examples of drugs and alternative forms of these drugs such as alternative salt forms, free acid forms, free base forms, and hydrates:

analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate);

antiasthamatics (e.g., ketotifen and traxanox);

antibiotics (e.g., neomycin, streptomycin, chloramphenicol, cephalosporin, ampicillin, penicillin, tetracycline, and ciprofloxacin);

antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline);

antidiabetics (e.g., biguanides and sulfonylurea derivatives);

antifungal agents (e.g., griseofulvin, ketoconazole, itraconizole, amphotericin B, nystatin, and candicidin);

antihypertensive agents (e.g., propranolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone);

antineoplastics (e.g., cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, tamoxifen, and piposulfan);

antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene);

immunosuppressive agents (e.g., cyclosporine, azathioprine, mizoribine, and FK506 (tacrolimus));

antimigraine agents (e.g., ergotamine, propranolol, isometheptene mucate, and dichloralphenazone);

sedatives/hypnotics (e.g., barbiturates such as pentobarbital, pentobarbital, and secobarbital; and benzodiazepines such as flurazepam hydrochloride, triazolam, and midazolam);

antianginal agents (e.g., beta-adrenergic blockers; calcium channel blockers such as nifedipine, and diltiazem; and nitrates such as nitroglycerin, isosorbide dinitrate, pentaerythritol tetranitrate, and erythrityl tetranitrate);

antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine);

antimanic agents (e.g., lithium carbonate);

antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine);

antiarthritic agents (e.g., phenylbutazone, sulindac, penicillamine, salsalate, piroxicam, azathioprine, indomethacin, meclofenamate, gold sodium thiomalate, ketoprofen, auranofin, aurothioglucose, and tolmetin sodium);

antigout agents (e.g., colchicine, and allopurinol);

anticoagulants (e.g., heparin, heparin sodium, and warfarin sodium);

thrombolytic agents (e.g., urokinase, streptokinase, and alteplase);

antifibrinolytic agents (e.g., aminocaproic acid);

hemorheologic agents (e.g., pentoxifylline);

antiplatelet agents (e.g., aspirin);

anticonvulsants (e.g., valproic acid, divalproex sodium, phenytoin, phenytoin sodium, clonazepam, primidone, phenobarbitol, carbamazepine, amobarbital sodium, methsuximide, metharbital, mephobarbital, mephenytoin, phensuximide, paramethadione, ethotoin, phenacemide, secobarbitol sodium, clorazepate dipotassium, and trimethadione);

antiparkinson agents (e.g., ethosuximide);

antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and);

agents useful for calcium regulation (e.g., calcitonin, and parathyroid hormone);

antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate);

antiviral agents (e.g., interferon alpha, beta or gamma, zidovudine, amantadine hydrochloride, ribavirin, and acyclovir);

antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin);

anti-infectives (e.g., GM-CSF);

bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate;

steroidal compounds, hormones and hormone analogues (e.g., incretins and incretin mimetics such as GLP-1 and exenatide, androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium);

hypoglycemic agents (e.g., human insulin, purified beef insulin, purified pork insulin, recombinantly produced insulin, insulin analogs, glyburide, chlorpropamide, glipizide, tolbutamide, and tolazamide);

hypolipidemic agents (e.g., clofibrate, dextrothyroxine sodium, probucol, pravastitin, atorvastatin, lovastatin, and niacin);

peptides;

proteins (e.g., DNase, alginase, superoxide dismutase, and lipase);

nucleic acids (e.g., sense or anti-sense nucleic acids encoding any therapeutically useful protein, including any of the proteins described herein, and siRNA);

agents useful for erythropoiesis stimulation (e.g., erythropoietin);

antiulcer/antireflux agents (e.g., famotidine, cimetidine, and ranitidine hydrochloride);

antinauseants/antiemetics (e.g., meclizine hydrochloride, nabilone, prochlorperazine, dimenhydrinate, promethazine hydrochloride, thiethylperazine, and scopolamine);

oil-soluble vitamins (e.g., vitamins A, D, E, K, and the like);

as well as other drugs such as mitotane, halonitrosoureas, anthrocyclines, and ellipticine.

A description of these and other classes of useful drugs and a listing of species within each class can be found in Martindale, *The Extra Pharmacopoeia,* 30th Ed. (The Pharmaceutical Press, London 1993), the disclosure of which is incorporated herein by reference in its entirety.

C. Dosage Forms

Any dosage form suitable for delivery to the skin may be used. The compositions may be in the form of films, depots, patches or neat liquids, creams, lotions.

In one embodiment, ILs are delivered to the skin surface by a drug delivery device containing a reservoir for holding the ILs. In a preferred embodiment, the reservoir also contains one or more drug(s).

In another embodiment, the ILs may be contained within a drug delivery device. A variety of different devices having a variety of different geometries and structures may be formed. For example, the device may be a multicompartment device, which also contains the ILs.

II. Uses for Compositions

The compositions described herein may be used for transdermal drug delivery.

The compositions may be applied to the surface of the skin to treat a disease or disorder of the skin, including but not limited to atopic dermatitis, acne, wound, rash, folliculitis, furunculosis, carbunculosis fungal infection, and other diseases of infectious origin.

In some embodiments, the components of the composition (e.g. cationic component, anionic component, and/or drug) are selected such that the drug to be delivered is delivered within the layers of the skin. This is particularly useful for the treatment of diseases or disorders of the skin, such as treatment of an infection, cut, burn, or rash.

In other embodiments, the components of the composition (e.g. cationic component, anionic component, and/or drug) are selected such that the drug to be delivered is transported through the skin.

In still other embodiments, the components of the composition may be selected such that they prevent transfer of a drug (or other substance) through the stratum corneum. In these embodiments, the composition may be applied to the surface of the skin to form a coating to protect the skin or treat large open wounds.

In some embodiments the compositions contain ILs in an effective amount to disrupt bacterial biofilms. In these embodiments the compositions may not include a drug to be delivered. For example, the composition may contain an ionic liquid that contains one cationic component and one anionic component, and does not contain a drug to be delivered in addition to the cationic and anionic components. This composition can be applied to a synthetic surface or a biological surface (e.g. the skin).

In some embodiments the compositions contain ILs in an effective amount to inhibit microbial growth on a synthetic surface. For example, the surface could be the surface of a medical device, such as an implantable medical device.

EXAMPLES

General Experimental Materials

Trihexyltetradecylphosphonium chloride, or CYPHOS 101 (CY101), was a gift from Cytec Specialty Chemicals (Niagara Falls, Ontario) and was purified prior to use by washing with 1 M sodium bicarbonate and water and extracting with hexanes until the UV-Vis absorption beyond 300 nm disappeared and the pH of 2 mL water did not change upon being shaken with 2 mL of the ionic liquid. CY101 was then dried at 80° C. under vacuum for 24 h.

Geranic acid was purified from the commercially available technical grade (Sigma-Aldrich, St. Louis, Mo.) by repeated (5-7×) recrystallization from a solution of 70 wt % geranic acid/30 wt % acetone at −70° C. Purity of products was assessed by 1H NMR spectroscopy and conductivity measurements.

Determination of Lipophilicity

A 250 mL volume of n-octanol was shaken with 100 mL of ddH$_2$O and left overnight. The saturated octanol was used to prepare 0.01 M solutions of each IL in 5 mL volumetric flasks, as well as 0.01 M solutions in water. For the choline-oleate and BZBN materials, the concentrations assayed were 0.0005 M and 0.0001 M, respectively, because the absorption at 0.01 M was too high for the detector. The BMP-NTf$_2$ IL was assayed at 0.2 M because the absorption at lower concentrations was below the acceptable limit of detection. Absorption maxima between 205 and 215 nm were observed in all cases.

A 4 mL portion of the IL solution was shaken with 4 mL of ddH$_2$O for 1 min, followed by 1 min of gentle centrifugation (1000 rpm, 129×g, Thermo IEC Centra CL2 centrifuge, 4-hole fixed angle rotor 804SF, Thermo Fisher Scientific, Waltham, Mass.) to obtain clean separation of the two layers. The absorption of the octanol layer and water layers were measured and compared with the absorbance of the stock solutions. Measurements were repeated three times and the distribution coefficients were reported as the average. The percent of IL in octanol was calculated as the absorbance of the octanol layer after extraction divided by the absorbance of IL in octanol before extraction. The water/octanol distribution coefficient was calculated as the logarithm of the percent of IL in octanol divided by the percent of IL in water.

Viscosity and DSC

Viscosity was measured on 1 mL samples with a Viscolab 3000 viscometer (Cambridge Viscosity, Medford, Mass.). Samples were heated to 90° C. and viscosity was recorded in 2 degree increments between 50 and 90° C. with 8 min equilibration at each temperature. Low-temperature differential scanning calorimetry (DSC) was performed on a DSC882e instrument (Mettler-Toledo Inc., Columbus, Ohio) under N$_2$ atmosphere over two complete scans of a temperature range of −60 to 120° C. with a ramp rate of 10° C. per minute and a sample size of 18-21 mg in an aluminum crucible.

Conductivity and Density

Determinations of conductivity were made on an ION450 benchtop meter (Radiometer Analytical) with a 2-pole electrode designed for use in viscous liquids (Radiometer Analytical CDC241-9) and calibrated with KCl. Conductivity was measured three times per sample on stirred 3 mL volumes of neat IL at 25° C. Density was measured three times per IL using a 1 mL volumetric flask and an analytical balance.

UV-Vis and NMR Spectroscopy

Absorption spectra were collected on a Hewlett-Packard 8453 diode array spectrophotometer (Agilent Technologies, Inc., Santa Clara, Calif.) in a 1 cm pathlength quartz cuvette. NMR datasets were collected on a 300 MHz Bruker instrument using sample concentrations of 50 mM in CDCl3.

Preparation of [PR$_4$][carboxylate] ILs

Preparation of PR$_4$-oleate

Ionic liquids containing the $[P(C_{14}H_{29})(C_6H_{13})_3]^+$ cation and the oleate anion were prepared via salt metathesis. To a 50 mL solution of sodium oleate (10.0 g, 0.035 mol) in chloroform was added a 50 mL solution of trihexyltetradecylphosphonium chloride (CY101, 18.39 g, 0.35 mol) in chloroform. Five portions of 50 mL water were added to the stirred solution and removed, after which a test of the removed water with silver nitrate was no longer positive for the presence of chloride. Solvent was removed from the chloroform layer and the resulting IL was dried in a vacuum oven at 80° C. for 48 h.

Physical characterization at 25° C.: solubility in water=trace; density=0.882 g/mL; conductivity=0.016 mS/cm; viscosity=299 cP.

Preparation of PR$_4$-hexanoate

To a solution of 1.46 g (0.011 mol) sodium hexanoate in 15 mL methanol was added 5.48 g (0.011 mol) CY101. The mixture was stirred for 15 mM, the methanol was removed by rotary evaporation, and the IL was washed in a separation funnel with 3×15 mL of water, until a test of the water with silver nitrate showed no chloride present. The IL was dried in a vacuum oven at 80° C. for 48 h.

Physical characterization at 25° C.: solubility in water=trace; density=0.912 g/mL; conductivity=0.488 mS/cm; viscosity=154 cP.

Preparation of PR$_4$-geranate

After recrystallization five times at −70° C. from 70% geranic acid/30% acetone, neat geranic acid (16.2 g, 0.096 mol) was added to sodium bicarbonate (8.09 g in 50 mL ddH2O) in a 500 mL round bottom flask and stirred until the pH was 8.5, gas evolution ceased, and the solution converged to a single phase. Neat CY101 (50 g, 0.96 mol) was added and the two-phase mixture was stirred for 2 h. The CY101 layer was washed three times with ddH2O and dried by rotary evaporation and in a vacuum oven at 65° C. for 48 h.

Physical characterization at 25° C.: solubility in water=trace; density=0.931 g/mL; conductivity=0.156 mS/cm; viscosity=122 cP.

Preparation of Other ILs

Preparation of Choline-NTf2

The synthesis of choline-NTf2 was performed as described by Nockemann et al. [1] and the density (1.5 g/mL), NMR (1H and 13C) and melting point (30° C.) were found to agree with the published values. Physical characterization at 25° C.: solubility in water=1.7 M; density=1.53 g/mL; conductivity=1.46 mS/cm; viscosity=125 cP.

Preparation of BMP-NTf2

The synthesis of 1-Butyl-1-methylpyrrolidinium (BMP)-bistriflimide (NTf2) (BMP-NTf2) was performed as described by MacFarlane, D. R., et al., "*Pyrrolidinium imides: A new family of molten salts and conductive plastic crystal phases,*" Journal of Physical Chemistry B, 103(20): 4164-4170 (1999) and modified as described Baker, S. N., et al., "*Fluorescence studies of protein thermostability in ionic liquids*", Chemical Communications, (8): 940-1 (2004).

Physical characterization at 25° C.: solubility in water=0.2 M; density=1.39 g/mL; conductivity=1.99 mS/cm; viscosity=72.7 cP.

Preparation of Bze-ZnCl2-BMP-NTf2

Two ionic liquids, BMP-NTf2 and benzethonium-Cl—(ZnCl2)2 were synthesized and then combined in a 50/50 wt % mixture by stirring at 80° C. for 2 h. The synthesis of benzethonium-Cl—$(ZnCl_2)_2$ was performed from a mixture of benzethonium chloride and two equivalents of anhydrous zinc chloride as described in Lovejoy, K. S., et al., "*Utilization of Metal Halide Species Ambiguity to Develop Amorphous, Stabilized Pharmaceutical Agents As Ionic Liquids*" Crystal Growth & Design, 12(11): p. 5357-5364 (2012) and subsequently combined with BMP-NTf2.

Physical characterization at 25° C.: solubility in water=0.2 M; density=1.40 g/mL; conductivity=0.026 mS/cm; viscosity=8176 cP.

Preparation of 1-hexyl-3-methylimidazolium chloride (HMIM-Cl)

As described for the butyl derivative in Wilkes, J. S., et al., "*Dialkylimidazolium Chloroaluminate Melts—a New Class of Room-Temperature Ionic Liquids for Electrochemistry*", Spectroscopy and Synthesis. Inorganic Chemistry, 21(3): 1263-1264 (1982), 1-methylimidazole (11.9 g, 0.122 mol) was refluxed with an excess of chlorohexane (20.98 g, 0.146 mol) for 3 hours or until the reaction was complete as tested by the absence of a blue color upon adding a few drops of the reaction mixture to an aqueous solution of Cu(SO4). Carson, L., et al., "*Antibiofilm activities of 1-alkyl-3-methylimidazolium chloride ionic liquids*", Green Chemistry, 11(4): p. 492-497 (2009). Chlorohexane was removed by rotary evaporation.

Physical characterization at 25° C.: solubility in water=0.7 M; density=1.005 g/mL; conductivity=0.340 mS/cm; viscosity=680 cP.

Preparation of [choline][carboxylate]$_2$ Deep Eutectic Solvents

Determination of Choline/Carboxylic Acid Ratio

To 3, 2, 1, 0.5, or 0.33 equivalents of choline bicarbonate (80 wt % solution) was added neat hexanoic acid (2 g, 0.007 mol) in a 20 mL scintillation vial. The mixture was stirred at room temperature until $CO_2$ evolution ceased. Solvent was removed by rotary evaporation at 60° C. for 20 min, and each product was dried in a vacuum oven for 48 h at 60° C. Melting point was determined by DSC as described and the preferred composition was determined to be the one with the lowest melting point.

Preparation of Choline Oleate

Deep eutectic solvents (DESs) containing two equivalents of carboxylate and one equivalent of choline were prepared by neutralizing choline bicarbonate. To two equivalents of neat oleic acid (9.34 g, 0.033 mol) in a 250 mL round bottom flask was added 3.41 g of an 80 wt % solution of choline bicarbonate (2.73 g, 0.0165 mol). A portion of 20 mL methanol was added to the mixture to improve stirring at room temperature and the stirring continued until no more $CO_2$ evolved. Solvent was removed by rotary evaporation at 60° C. for 20 min, and the product was dried in a vacuum oven for 48 h at 60° C.

Physical characterization at 25° C.: solubility in water=0.2 M; density=0.98 g/mL; conductivity=0.087 mS/cm; viscosity=880 cP.

Preparation of Choline Hexanoate

To two equivalents of neat hexanoic acid (16 g, 0.138 mol) in a 500 mL round bottom flask was added 14.22 g of an 80 wt % solution of choline bicarbonate (11.38 g, 0.069 mol). The mixture was stirred at room temperature until no more $CO_2$ evolved. Solvent was removed by rotary evaporation at 60° C. for 20 min, and the product was dried in a vacuum oven for 48 h at 60° C.

Physical characterization at 25° C.: solubility in water=0.5 M; density=1.01 g/mL; conductivity=0.816 mS/cm; viscosity=181 cP; melting point=−94° C.

Preparation of Choline Geranate

To two equivalents (9.88 g, 0.059 moles) of neat geranic acid, recrystallized 5× at −70° C. from 70% geranic acid/30% acetone, in a 500 mL round bottom flask was added one equivalent of choline bicarbonate (80 wt % solution, 6.06 g, 0.029 mol). The mixture was stirred at room temperature until no more $CO_2$ evolved. Solvent was removed by rotary evaporation at 60° C. for 20 min, and the product was dried in a vacuum oven for 48 h at 60° C.

Physical characterization at 25° C.: solubility in water=0.5 M; density=0.990 g/mL; conductivity=0.0431 mS/cm; viscosity=1345 cP.

Preparation of Choline Malonate

Because malonic acid is a dicarboxylic acid, one equivalent of was used with one equivalent of choline chloride. To one equivalent of malonic acid (2.76 g, 0.027 mol) in a 250 mL round bottom flask was added one equivalent of choline chloride (3.70 g, 0.027 mol). The mixture was stirred 24 h at room temperature, and the material was filtered through a Pasteur pipette containing about 0.5 mL of celite using ~5 psi N2, and then dried in a vacuum oven for 24 h at 45° C. A gas was observed to evolve rapidly from the material upon heating to about 80° C.

Physical characterization at 25° C.: solubility in water=miscible; density=1.266 g/mL; conductivity=0.429 mS/cm; viscosity=920 cP.

Preparation of Non-Carboxylate DESs

Preparation of Urea-Choline

As described in Abbott, A. P., et al., "*Novel solvent properties of choline chloride/urea mixtures*", Chem. Commun (Cambridge, U.K.), (1): 70-71 2003), two equivalents of urea (10 g, 0.167 mol) were mixed with one equivalent of choline chloride (11.6 g, 0.083 mol) in a scintillation vial under argon atmosphere. The material was dried for 24 h in a vacuum oven at 60° C. The DES was heated to 30° C. prior to use.

Physical characterization at 25° C.: solubility in water=miscible; density=1.21 g/mL; conductivity=0.580 mS/cm; viscosity=1390 cP.

Table 2 lists the abbreviations, starting cationic and anionic components and molar ratios used for the ILs that were tested.

TABLE 2

Abbreviations, starting components, and molar ratios for ILs

| Abbreviation | Cation | Anion | Molar Ratio (Cation:Anion) |
|---|---|---|---|
| LANL-1 | BMP | Bistriflimide | 1:1 |
| LANL-2 | Bze, BMP | $ZnCl_2$, Bistriflimide | 1:1:1:1 |
| LANL-5 | Choline | Disodium Malonate | 1:1 |
| LANL-6 | Choline | Urea | 1:2 |
| LANL-7 | HMIM | Chloride | 1:1 |
| LANL-12 | Choline | Bistriflimide | 1:1 |
| LANL-13 | Choline | Hexanoic Acid | 1:2 |
| LANL-14 | Choline | Oleic Acid, Hexanoic Acid | 2:2:2 |
| LANL-19 | $PR_4$ | Sodium Oleate | 1:1 |
| LANL-20 | $PR_4$ | Sodium Hexanoate | 1:1 |
| LANL-21 | Choline | Sodium Geranate | 1:2 |
| LANL-22 | $PR_4$ | Sodium Geranate | 1:1 |

Biological Methods

Cell Culture and Exposure.

Normal human bronchial epithelial (NHBE) cells were purchased (Lonza, Walkersville, Md.) and cultured using bronchial epithelial cell growth media (BEGM, Clonetics Bullet Kit, Lonza, Walkersville, Md.) on 100 mm tissue culture treated Petri dishes (Santa Cruz Biotechnologies, Santa Cruz, Calif.) coated with 50 µg/mL type I rat tail collagen (BD Biosciences, Bedford, Mass.). Cells were stored in an incubator with a humidified atmosphere at 37° C. and 5% $CO_2$. Cells were fed two times weekly and passaged via trypsinization. Experimentation was performed in triplicate on cells harvested from passages 3 to 7.

NHBE cells were plated in 96-well tissue culture plates at a concentration of $1.5 \times 10^4$ cells/well in a volume of 200 µL and allowed to acclimate overnight. On the day of experimentation, treatment plates were prepared using stock ionic liquid diluted in BEGM and then serially diluted 3-fold for a total of 7 concentrations. The 96-well plates containing cells were then aspirated and the treatments (150 µL/well) were carefully transferred from the prep plate to the cells. Cells were exposed to the ionic liquids for 24 hours. Two hours prior to the end of the exposure time, positive control cell wells were aspirated, and a solution of 1% Triton-100 (150 µL/well) was added.

Proliferation and Cytotoxicity Assay.

After 24 h of exposure, 75 µL of cell culture supernatant were taken from each well and transferred to a new flat bottom plate for later analyses of lactate dehydrogenase (LDH) activity. Plates were covered and stored at 4° C. until analysis was performed.

To assess cellular proliferation, water-soluble tetrazolium (WST-1) reagent (Clontech, Mountain View, Calif.) was added directly to cells, at a 1:10 dilution of the remaining media volume (7.5 µL of WST-1 reagent was added per 75 µL remaining cell culture media). NHBE cells exposed to media only and 1% Triton in BEGM were included as controls. Ionic liquid controls at the highest concentrations tested were included in wells without cells to rule out ionic liquid/assay reagent interference. Absorbance was read on a Biotek plate reader at 440 nm with a reference wavelength of 600 nm.

The amount of LDH in supernatants can be measured and used as an indirect measure of cell membrane permeability. Thus, the cytotoxic effects of ionic liquids upon NHBE cells was evaluated by measuring LDH activity using a LDH cytotoxicity kit (Clontech, Mountain View, Calif.) as outlined in Martin, et al., "*Impact of physicochemical properties of engineered fullerenes on key biological responses*", Toxicology and Applied Pharmacology, 234(1): 58-67 (2009).

NHBE cells exposed to media only or 1% Triton-100 in BEGM served as controls. QD controls at the highest concentrations tested were included in wells without cells to determine if ionic liquids themselves interfere with LDH reaction mix. Absorbance was read on a Biotek plate reader at 490 nm with a reference wavelength of 600 nm.

Measurement of Skin Transport 3H-labeled Mannitol and Cefadroxil were obtained from American Radiolabeled Chemicals, Inc. and Moravek, respectively. FDCs were used to assess the transport enhancement of ionic liquids using a previously established protocol. Karande, et al., "*Discovery of transdermal penetration enhancers by high-throughput screening*", Nat Biotechnol, 22(2): 192-7 (2004). Briefly, the acceptor chamber was filled with degassed PBS and a small stir bar added. Thawed porcine skin was clamped in place between the acceptor and donor chambers with the SC facing up. Care was taken to ensure no air bubbles resided in the acceptor chamber. Ionic liquids or PBS (control) were spiked with 3H-labeled drug (Mannitol and Cefadroxil) to a final concentration of 10 µCi/ml. 300 µL of donor solution was added to the donor chamber and incubated in contact with the SC for 24 hr, at 37° C., with stirring.

After 24 hr, the donor solution was removed, and the skin was thoroughly washed and dried.

SC was separated from epidermis by tape stripping. Ten tape strips were performed in an identical fashion, with each tape corresponding to 1 SC "layer". Ten strips were assumed to remove the majority of the SC. Epidermis was separated from dermis with a razor blade, and the acceptor solution was collected from the acceptor chamber. Samples from each tissue layer and acceptor solution were dissolved in Soluble (Perkin Elmer, Waltham, Mass.) overnight and the concentration of radiolabeled solute was measured using a scintillation counter (Packard Tri-Carb 2100 TR, Meriden, Conn.).

Bacterial Biofilm Growth in Innovotech MBEC Plates

*96-well plates used for Rinse, Challenge, Wash, and Sonication were Costar flat-bottom polystyrene, with lid. Cat #3370. 96-well plates Day 1:
  pm: Use a glycerol stock aliquot to streak a fresh LB agar plate. Streak for isolated colonies. Incubate overnight at 37° C.

Day 2:
  am: Remove growth agar plate from incubation and inspect for contamination. Store the agar plate at room temperature or 4° C., until later in the day.
  pm: Use a single colony from the growth plate to inoculate 5 mL LB liquid culture. Incubate overnight with vigorous shaking (225-250 rpm) at 37° C.

Day 3:
  am: Inoculate fresh 5 mL LB liquid culture with 50 uL from overnight liquid culture (1:100 dilution). Incubate at 37° C. with vigorous shaking until culture reaches log phase growth (~0.5 OD). This is roughly 3 hours for most laboratory bacterial strains.

Use the log phase growth culture to set up the biofilm growth plate by diluting the culture 1:50 into fresh LB media, using a suitable total volume to inoculate the number of wells and/or plates required. Add 200 uL diluted culture to each well. Place the MBEC plate lid (with pegs) on top of the well plate, and seal the edges with parafilm. This is the best way to prevent evaporation from the wells. Incubate the plate, 225 RPM, for 24 hours at 37° C.

Day 4:

At 24 hours biofilm growth, remove planktonic cells/media from the biofilms by placing the MBEC peg lid onto a fresh 96-well plate with 200 uL/well of fresh LB media. Discard the well plate containing planktonic cells/media.

If growing biofilms for greater than 24 hours, after each 24 hour period of incubation, the planktonic cells/media should be removed and the biofilms "fed" with fresh media.

Once biofilms are ready to be challenged or visualized, a 200 uL gentle LB media "rinse" should be performed (after planktonic cell/media removal) to remove cells that are loosely associated with the biofilm. This is accomplished by briefly placing the peg-attached biofilms onto a 96-well plate with 200 uL fresh LB.

Bacterial Biofilm Challenge with Ionic Liquids. A Modification of the ©Innovotech MBEC HTP Assay Challenge Plate Setup Step I: Biofilms grown on MBEC pegs were rinsed briefly, at room temperature, to remove planktonic and loosely adhered bacterial cells. The MBEC peg lid was placed briefly onto a 96-well plate with 200 uL/well LB. Planktonic cells were discarded from both the biofilm growth plate and the rinse plate (not the MBEC peg lid) into a decontamination bucket with 10% bleach.

Step II: The MBEC peg lid was then situated onto the challenge plate. Ionic liquids and control solutions were added in triplicate wells in an alternating arrangement at 200 uL/well. In general 3-4 ionic liquids, component controls for each, and positive (LB) and negative (LB/10% bleach) controls, comprised each challenge plate. Viscous ionic liquids were heated to 60° C. prior to challenge plate setup. The edges of the plate/lid were covered with parafilm.

Step III: The biofilms were challenged at 37° C., 225 RPM.

Assay Processing

Step IV: Following ionic liquid challenge, the biofilms were washed with 200 uL/well LB, briefly, at room temperature, and then set aside for dilution.

Step V: The biofilms were then placed onto another 96-well plate with 200 uL/well LB. 200 uL LB was added to all wells of the plate, regardless of challenge plate layout. The edges of the plate/lid were covered with parafilm; and the wash plate was set aside for dilution. The biofilms were sonicated, at room temperature, using a Misonix® 3000 fitted with a microplate horn. DI water is added to the horn so that the water level touches the bottom of the plate. Sonication proceeds for 1 hour at an output level of 0.5, 3 seconds on, 3 seconds off. (Note: total sonication time is therefore 30 minutes).

Step VI: While sonication proceeded, sample wells from the challenge and wash plates were transferred to the "A" rows of 96-well dilution plates (which were set up in advance), as follows:

a. Challenge plate: 100 uL per challenge well was transferred to row "A" of a dilution plate, which contained 100 uL sterile 1×PBS.

Rows B-H contained 180 uL sterile Millipore water. Challenge solutions/PBS was mixed by pipetting up and down at least 10×.

b. Wash plate: 200 uL (total volume) per wash well was transferred to row "A" of a dilution plate. Rows B-H contained 180 uL sterile Millipore water.

Step VII: After challenge and wash samples were transferred to row "A" of their respective dilution plates, each well was serially diluted 1:10, vertically. 20 uL/well was transferred into 180 uL, using a multichannel pipettor, and mixed 10×. Row "H" was a 10-7 dilution of the sample in row "A".

Step VIII: The sonicated samples were transferred and diluted in the same way as the wash samples.

Step IX: Remaining liquid volume was discarded from the challenge and properly decontaminated and disposed.

Recovery Plating

Step X: After all samples were diluted, dilutions were plated onto large LB agar plates (plates were at room temperature). Using an the concentrated (A), 10-2 (C), 10-4 (E), and 10-6 (G) dilutions of one row were mixed 3-5× using a pipettor (8-channel pipettor with a pipette tip on every other position); then 15 uL spots were transferred to large agar plate. This was repeated for the 10-1 (B), 10-3 (D), 10-5 (F), and 10-7 (H) dilutions.

Up to six samples, diluted to 10-7, each (resulting from 2 samples in triplicate) were plated onto one large agar plate.

Step XI: The spots were allowed to dry so that they did not run together, prior to inverting the agar plates. The plates were covers with parafilm, and incubated overnight at 37° C., inverted.

Analysis

Step XII: Agar plates were removed from incubation. For each sample dilution set, colonies were counted in spots that contain 20-200 colonies. The number of colonies and dilution factor was recorded.

Step XIII: Then cfu/mL was calculated as follows:

a. Challenge samples: (number of colonies)×(dilution factor)/0.015 mL×2 b. Wash/sonication samples: (number of colonies)×(dilution factor)/0.015 mL

Step XIV: The average cfu/mL was calculated for triplicates.

Step XV: The standard deviation for the population (the population=triplicates) was calculated (e.g. stdev.p in Excel).

Repeat

Step XVI: The Challenge assay was repeated, beginning with biofilm growth. The average cfu/mL and stdev.p for the duplicate growth/challenge assay was calculated, and then the average cfu/mL and stdev.p for all 6 samples resulting from duplicate growth/challenge assays was calculated.

Results and Discussion

Lipophilicity

Table 3 provides lipophilicity date for a variety of ILs in terms of their octanol/water partition coefficients.

TABLE 3

Lipophilicity data for ILs

| | log $P_{o/w}$ | percent in octanol | concentration of assay (M) |
|---|---|---|---|
| BMP-NTf2 (1) | −0.40 | 20% +/− 7% | 0.2 |
| Bze-ZnCl2-BMP-NTf2 (2) | 1.34 | 96 +/− 6% | 0.0001 |
| choline malonate (5) | −0.26 | 35 +/− 5% | 0.01 |
| urea-choline (6) | −0.51 | 24 +/− 8% | 0.01 |
| HMIM-Cl (7) | 0.04 | 52 +/− 9% | 0.01 |
| choline-NTf2 (12) | 0.31 | 67 +/− 9% | 0.05 |
| choline hexanoate (13) | 0.03 | 51 +/− 2% | 0.01 |
| choline oleate (14) | 1.32 | 95 +/− 3% | 0.0005 |
| [PC$_{14}$H$_{29}$(C$_6$H$_{13}$)$_3$][oleate] (19) | 1.14 | 93 +/− 2% | 0.01 |
| [PC$_{14}$H$_{29}$(C$_6$H$_{13}$)$_3$][hexanoate] (20) | 0.26 | 65 +/− 14% | 0.01 |
| choline geranate 1:2 (21) | 0.28 | 66 +/− 3% | 0.05 |
| [PC$_{14}$H$_{29}$(C$_6$H$_{13}$)$_3$][geranate] (22) | 0.86 | 88 +/− 6% | 0.01 |
| mineral oil | 0.95 | 90 +/− 3% | 0.01 |

The lipophilicity of the materials under consideration was determined in terms of their water-octanol distribution coefficients. The oleic acid/choline DES and the Bze-ZnCl$_2$—BMP-NTf$_2$ IL partitioned most efficiently into octanol, with 95% and 96% of the DES moving into the octanol layer after 1 min of agitation. Bze-ZnCl$_2$-BMP-NTf$_2$ contains a 1:1 by weight mixture of BMP-NTf$_2$ and a Bze-(ZnCl$_2$)$_2$ IL made from two equivalents of zinc chloride and one equivalent of benzethonium chloride. Lovejoy, K. S., et al., "*Utilization of Metal Halide Species Ambiguity to Develop Amorphous, Stabilized Pharmaceutical Agents As Ionic Liquids*", Crystal Growth & Design, 12(11): 5357-5364 (2012). The reason for the large difference between the log Po/w of BMP-NTf (−0.4) and that of BZBN (1.34) is that BMP-NTf$_2$ formed a third phase when in contact with water and octanol. At a starting concentration of 0.2 M in octanol, the percentage of BMP-NTf$_2$ in the water phase was 51% and the percentage not incorporated in octanol or water was 29%. Lipophilicity can be referenced to other accounts, specifically of choline-naphthenic "ILs", which actually are 1:1 from choline hydroxide. Yu, Y., et al., "*Biodegradable naphthenic acid* ionic liquids: synthesis, characterization, and quantitative structure-biodegradation relationship", Chem.-Eur. J., 14(35): p. 11174-11182 (2008).

Proliferation and Cytotoxicity

Table 4 provides WST results after 24 hr. In the case where lower limits are given, the solubility of the material precluded a proper $IC_{50}$ value.

TABLE 4

WST Results for ILs

| | $IC_{50}$ at 24 h (mM) |
|---|---|
| BMP-NTf2 | >>2 |
| urea-choline | >10 |
| choline-malonate | >>2 |
| HMIM-Cl | 10.03 |
| choline-hexanoate | 4.57 |
| chol-NTf2 | 1.7 |
| chol-ol/chol-hex | 1.5 |
| choline oleate | 0.034 |
| BZBN | 0.013 |

Cytotoxicity in Primary Human Cells

The toxicity of the materials in primary human cells was tested in normal human bronchial epithelial (NHBE) cells. This study was performed with IL and DES dilutions, not neat ILs/DESs, because it was intended to model toxicity upon absorption into the bloodstream. All materials were tested at concentrations of 2.0, 0.8, 0.3, 0.1, 0.05, 0.02, and 0.008 mM. Because of their high solubility in the culture medium, HMIM-Cl and choline-hexanoate were also tested at concentrations up to 500 mM and 30 mM, respectively. The most toxic materials were choline oleate (IC50=0.034 mM) and BZBN (IC50=0.013 mM) and the least toxic materials were urea-choline (IC50>10 mM) and HMIM-Cl (IC50=10 mM).

The toxicity of the solubilized ionic liquids was found to correspond well with the toxicity of the individual cation and anion components. Specifically, the more toxic components (benzethonium chloride and oleic acid) give rise to toxic DESs and ILs and the less toxic components (choline chloride and urea) produce a less toxic DES. Considering NHBE cell toxicity as well as biofilm efficacy results, choline-hexanoate, choline malonate, and HMIM-Cl had the largest "therapeutic windows." They were effective when used neat against biofilms, and have low toxicity to human primary cells in culture medium. This may be important for treating large open wounds where IL dissolution occurs rapidly. Alternatively, ILs that are toxic to cells after dissolution may be used topically or in situations where dissolution of the IL is slower. Ionic liquids that were very toxic to primary human cells in solution, including choline oleate and BZBN, also partitioned well into octanol, a trend that is also documented in toxicological literature.

Applied neat, these results may suggest that dissolution for toxic materials may be very slow limiting toxicity even on large open wounds. Materials that had low toxicity to human cells also partitioned poorly into octanol, as was found for urea-choline, choline malonate, and BMP-NTf$_2$.

Viscosity, Density, Conductivity, and Ionic Strength

Viscosity, Conductivity, and calculations of molarity and ionic strength for various ILs are provided in Table 5.

TABLE 5

ILs Viscosity, Conductivity, Molarity, and Ionic Strength

| IL (corresponding number) | viscosity (cP) | density (g/mL) | conductivity (mS/cm) | molarity (M) | ionic strength (M) | molecular weight |
|---|---|---|---|---|---|---|
| BMP-NTf2 (1) | 72.72 | 1.39 | 1.99 | 3.28 | 3.28 | 422.4 |
| Bze-ZnCl2-BMP-NTf2 (2) | 8176 | 1.40 | 0.026 | 0.97 | 2.44 | 1439 |
| choline malonate (5) | 920.1 | 1.27 | 0.429 | 5.20 | 5.20 | 243.7 |
| urea-choline (6) | 1386$^a$ | 1.21 | 0.580$^a$ | 4.65 | 2.32 | 259.7 |
| HMIM-Cl (7) | 679.5 | 1.01 | 0.340 | 4.96 | 4.96 | 202.7 |
| choline-NTf2 (12) | 125 | 1.54 | 1.460 | 4.40 | 4.40 | 348.9 |
| choline hexanoate (13) | 180.9 | 1.01 | 0.816 | 3.02 | 3.02 | 334.5 |
| choline oleate (14) | 162.3$^b$ | 0.98 | 0.0871$^b$ | 1.47 | 1.47 | 667.1 |
| [PC$_{14}$H$_{29}$(C$_6$H$_{13}$)$_3$][oleate] (19) | 300 | 0.882 | 0.0162 | 1.15 | 1.24 | 765.27 |
| [PC$_{14}$H$_{29}$(C$_6$H$_{13}$)$_3$][hexanoate] (20) | 154 | 0.912 | 0.488 | 1.63 | 1.63 | 559.02 |
| choline geranate 1:2 (21) | 1345 | 0.990 | 0.0431 | 2.26 | 3.39 | 438.63 |
| [PC$_{14}$H$_{29}$(C$_6$H$_{13}$)$_3$][geranate] (22) | 122.3 | 0.931 | 0.156 | 1.43 | 1.43 | 651.09 |
| mineral oil | 35 | 0.80 | 0.000 | 2.00 | 0.00 | 400.0 |

Ionic liquids produced with tetradecyltrihexylphosphonium as the cation result in viscosities of 300, 154, and 122 cP, all of which are higher than that of the parent IL, tetradecyltrihexylphosphonium chloride, but in the same order of magnitude. This large cation determines the viscosity of ILs made from a wide range of anions. Del Sesto, R. E., et al., "Tetraalkylphosphonium-based ionic liquids", Journal of Organometallic Chemistry, 690(10): 2536-2542 (2005). The deep eutectic solvents (DES) made from choline and two equivalents of carboxylic acid had viscosities ranging from 162 cP for choline oleate to 1390 cP for urea-choline, suggesting that the carboxylic acid component is more important than the choline component in determining viscosity. The viscosity of urea-choline at 40° C. was 170 cP and matched the literature value at 40° C. of 169 cP.

Abbott, A. P., et al., "*Design of improved deep eutectic solvents using hole theory*", ChemPhysChem, 7(4): p. 803-806 (2006).

Conductivities of these DESs ranged from 0.04 mS/cm for choline geranate to 0.816 mS/cm for choline hexanoate.

The densities of choline-based DESs formed with two equivalents of carboxylate ranged from 0.98 g/mL for choline oleate to 1.27 g/mL for choline malonate. These densities are similar to those measured for the 2/1 glucose/choline DES of 1.27 g/mL. Hayyan, A., et al., "*Glucose-based deep eutectic solvents: Physical properties*", Journal of Molecular Liquids, 178: 137-141 (2013). The densities of known ionic liquids, BMP-NTf$_2$, urea-choline, and choline-NTf$_2$ matched literature values, as indicated in the synthetic methods section.

Skin Transport

Figure 2A:
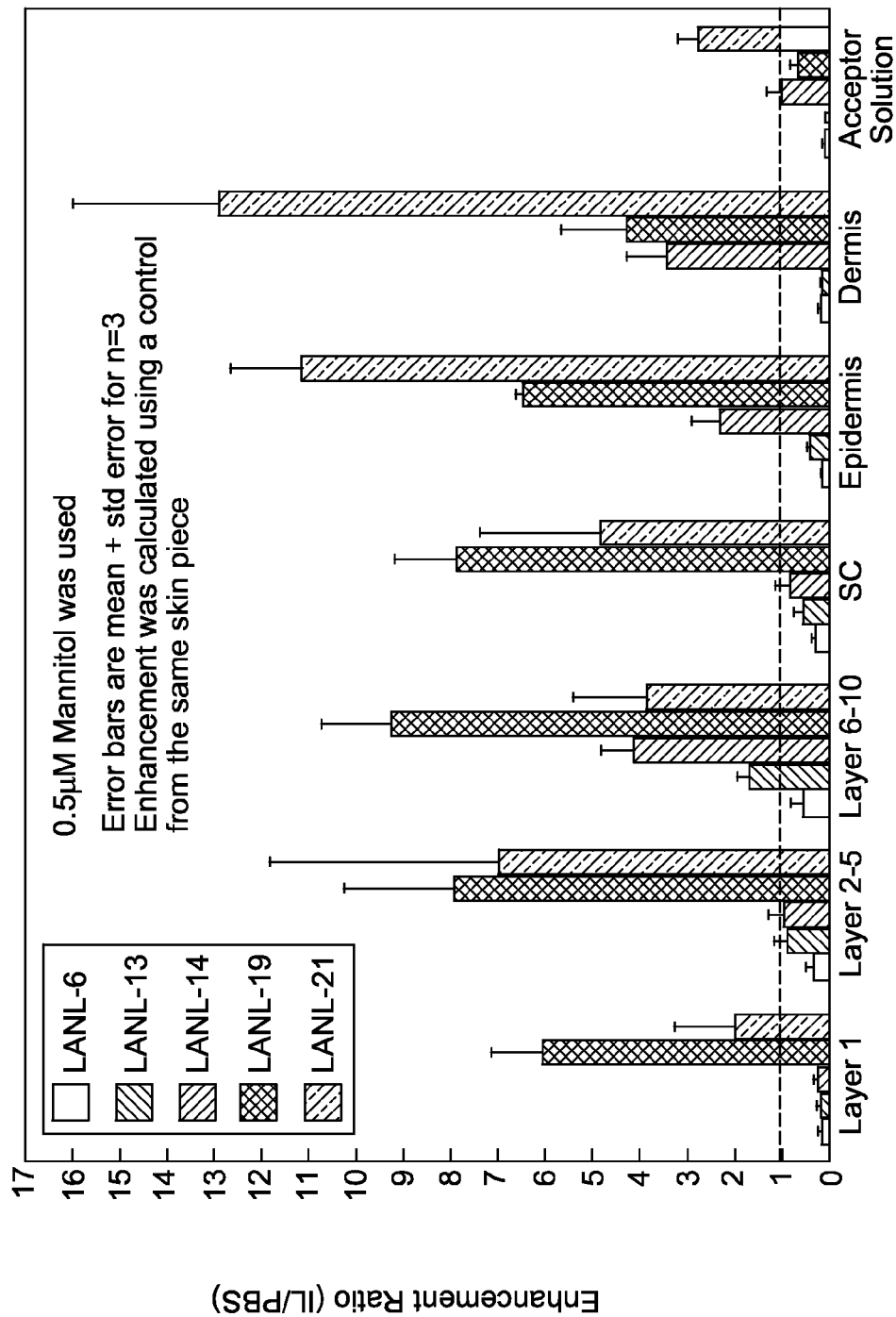
FIGS. 2A and 2B are bar graphs of Transport enhancement (relative to PBS control) into porcine skin by ionic liquids.

The transport enhancement of a panel of ionic liquids (ILs) listed in Table 2 was tested. The IL panel was first screened using 3H-Mannitol. The results are illustrated in FIG. 2A.

Figure 2B:
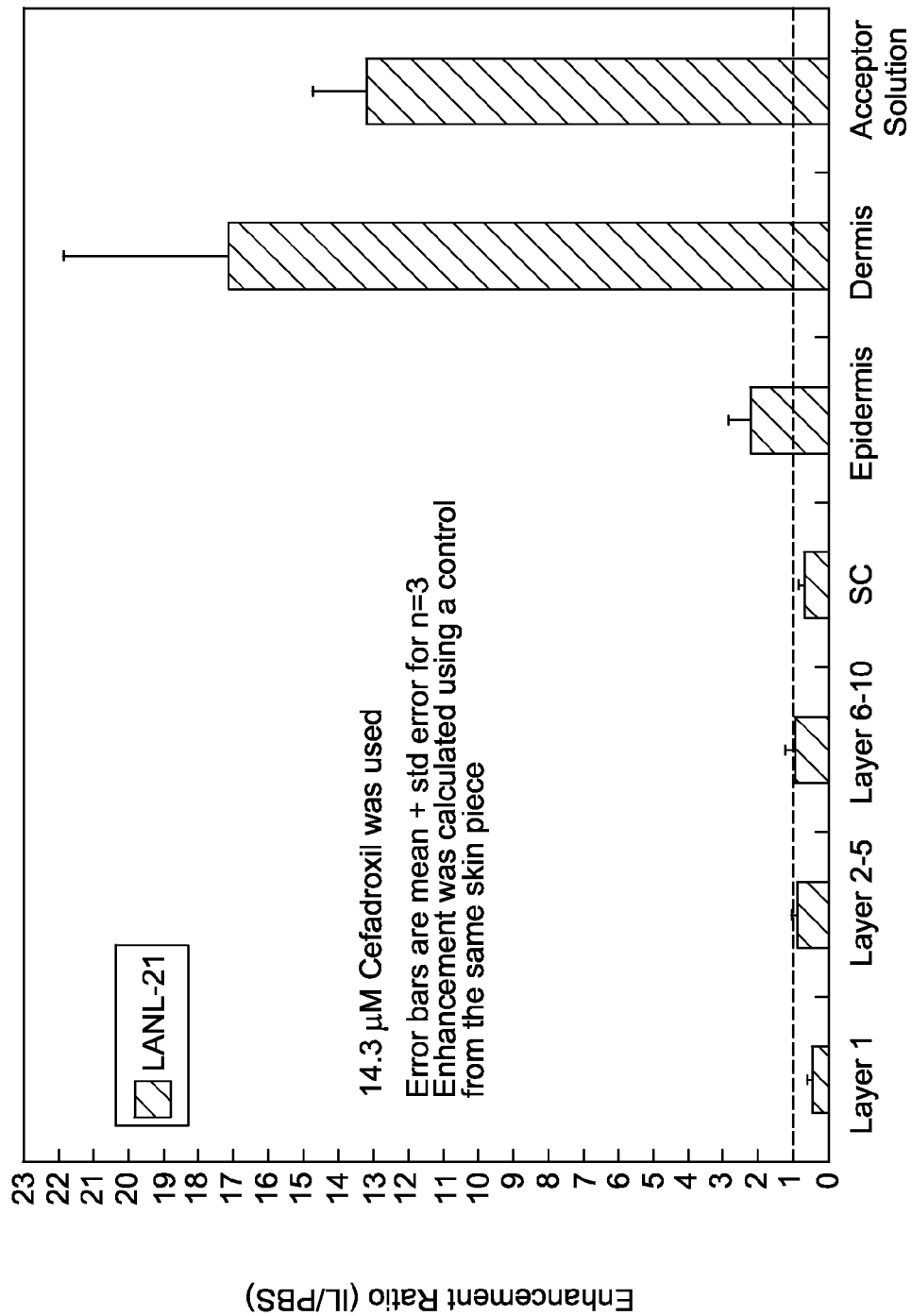
Figure 3:
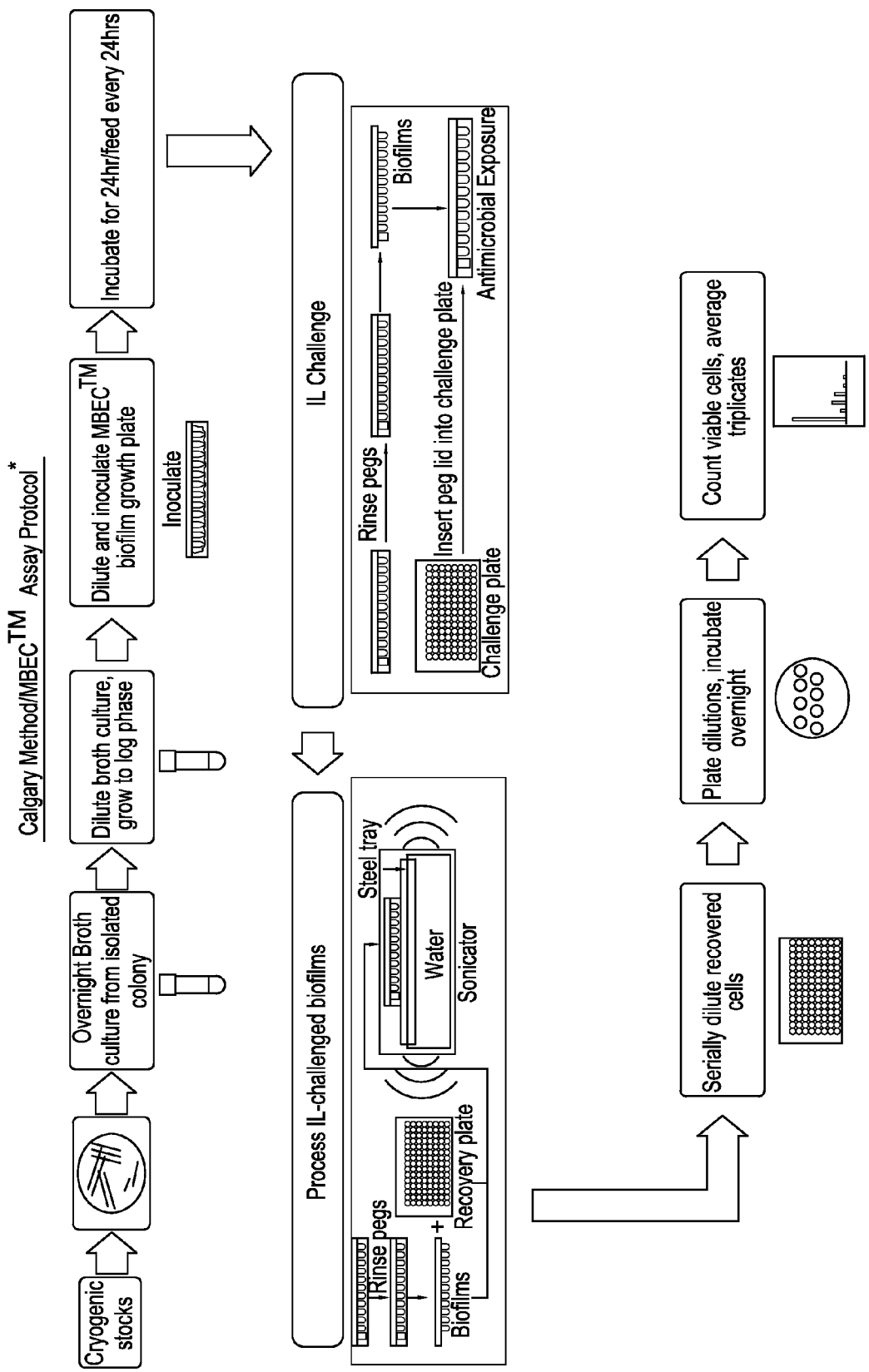
FIG. 3 is a schematic showing the Bacterial biofilm growth, IL challenge, and assay processing steps. MBEC™ HTP Assay plates were used for growing biofilms. A modified version of the MBEC™ HTP Assay protocol was used. ©Innovotech, Inc., Edmonton, AB, Canada.

Three distinct transport regimes emerged depending on the IL employed: 1) Drug retention in the donor solution. 2) Enhanced localization and retention within the SC, epidermis, and dermis. 3) Enhanced transdermal penetration through all layers of the skin and into the acceptor solution. In particular, LANL-6 and LANL-13 inhibited drug permeation into the SC. LANL-14 enhanced transport up to 5 fold into the deep tissue layers while showing no additional loss to the acceptor solution. LANL-19 enhanced transport 5-10 fold into all layers of the skin. Similar to LANL-14, no additional loss of solute to the acceptor solution was observed. LANL-21 enhanced penetration through all layers of the skin 5-15 fold and also enhanced partitioning into the acceptor solution. Moreover, when spiked with a model antibiotic, Cefadroxil, partitioning into the dermis and acceptor solution was 15-20 times greater than the control (PBS). See FIG. 2B. LANL-14, 19, 20, and 22 were tested as well and all showed similar total drug enhancement.

Biofilm Efficacy

Figure 4A:
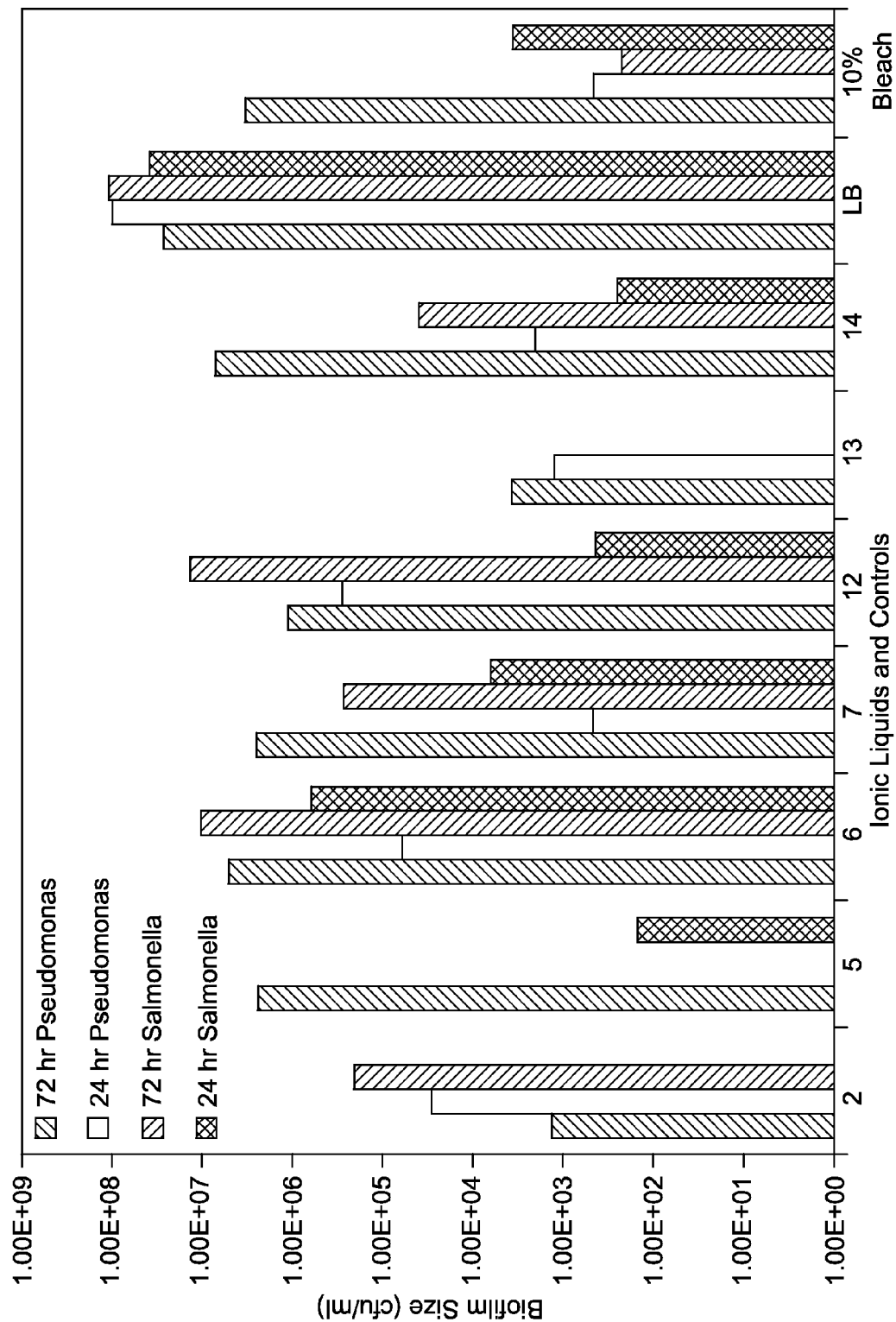
FIGS. 4A-C are bar graphs of biofilm size (cfu/ml) following 2 hour IL challenge, sonication and recovery. Materials tested were LANL-2, LANL-5, LANL-6, LANL-7, LANL-12, LANL-13, LANL-14, LB media (positive control), 10% bleach (negative control).
Figure 4B:
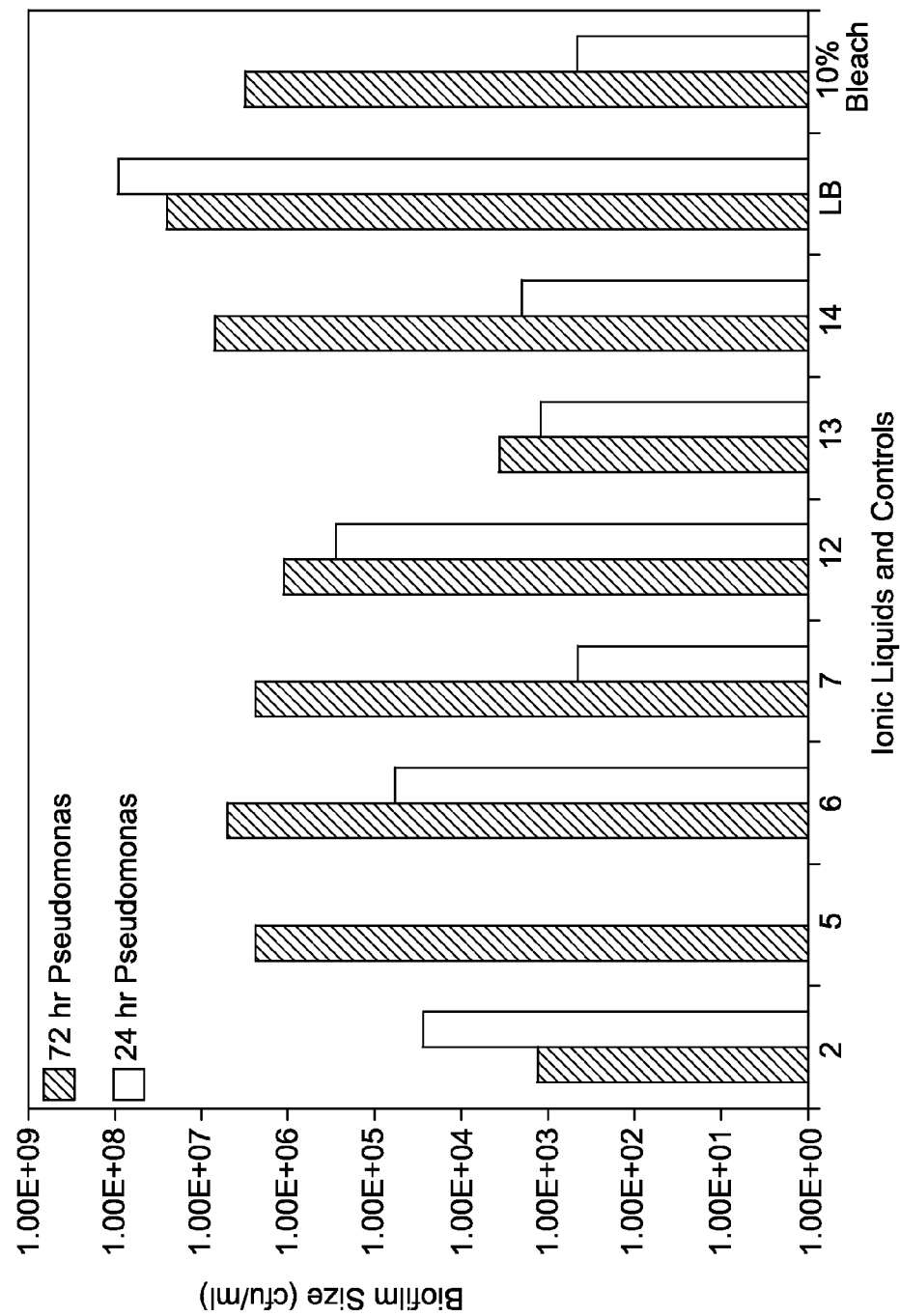
Figure 4C:
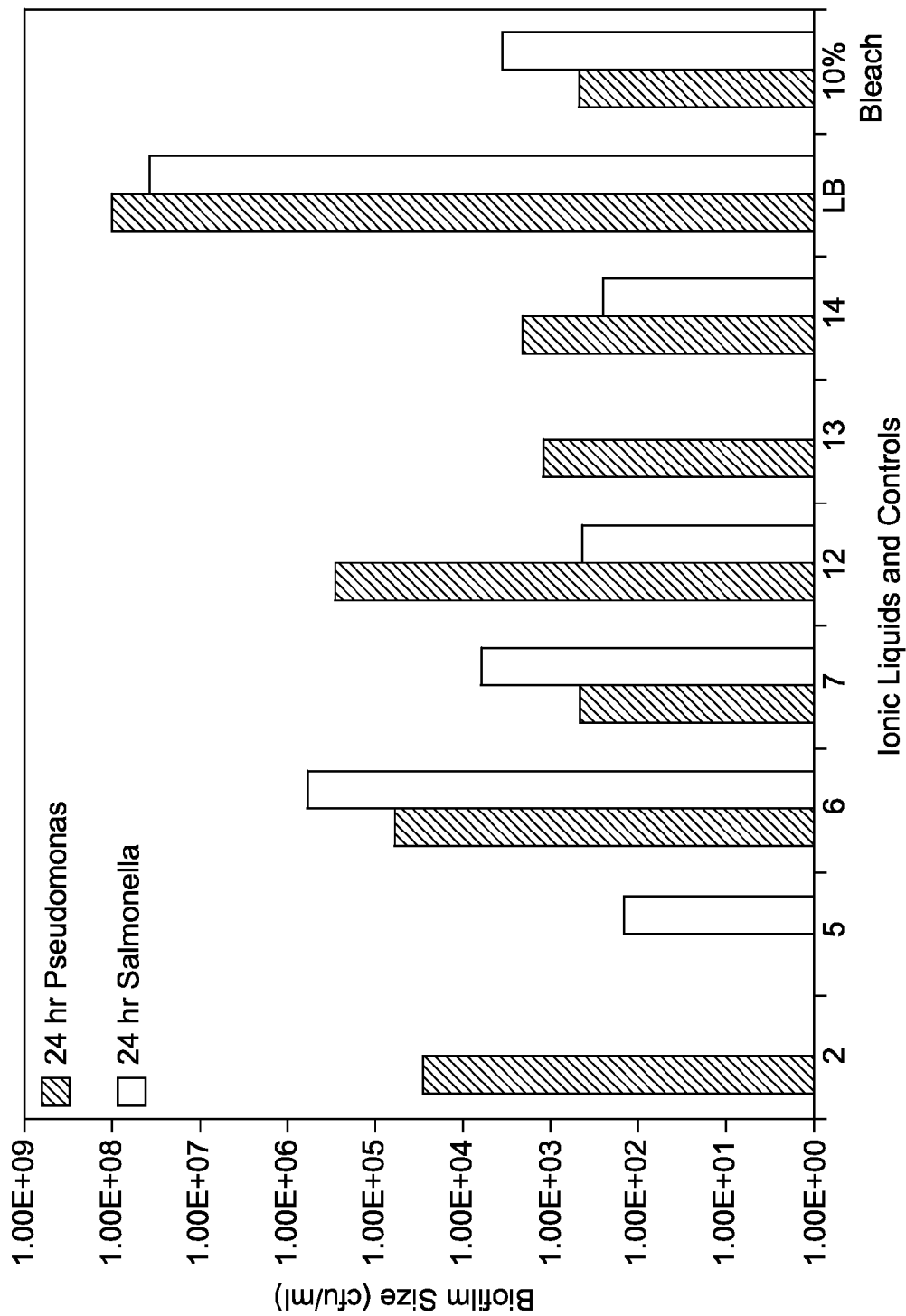
Figure 5A:
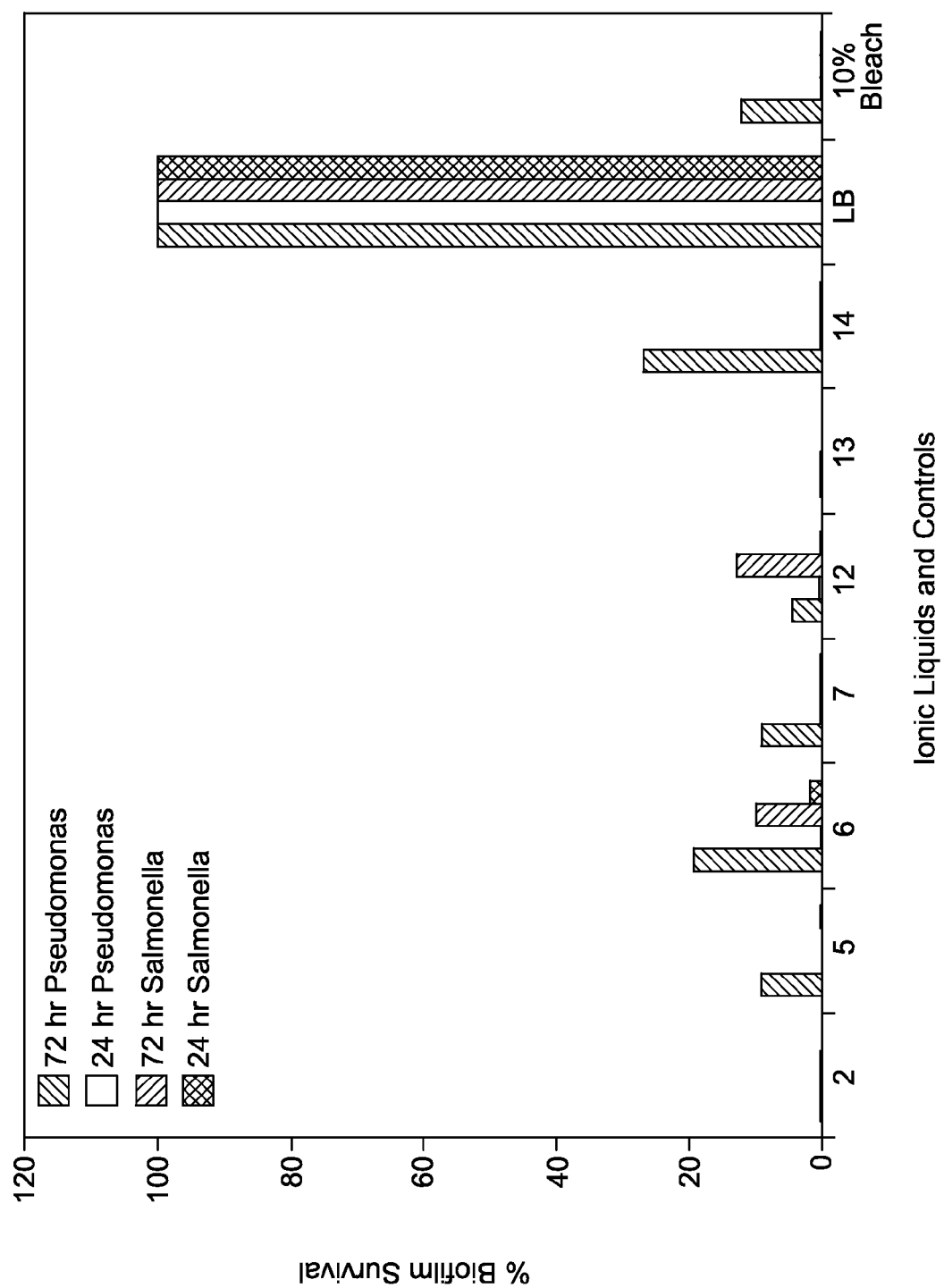
FIGS. 5A-5C are bar graphs of the percentage of surviving cells following 2 hour IL challenge, sonication, and recovery. LB (positive control)=100%. Average percent survival for n=6. Materials tested were LANL-2, LANL-5, LANL-6, LANL-7, LANL-12, LANL-13, LANL-14, LB media (positive control), 10% bleach (negative control).
Figure 5B:
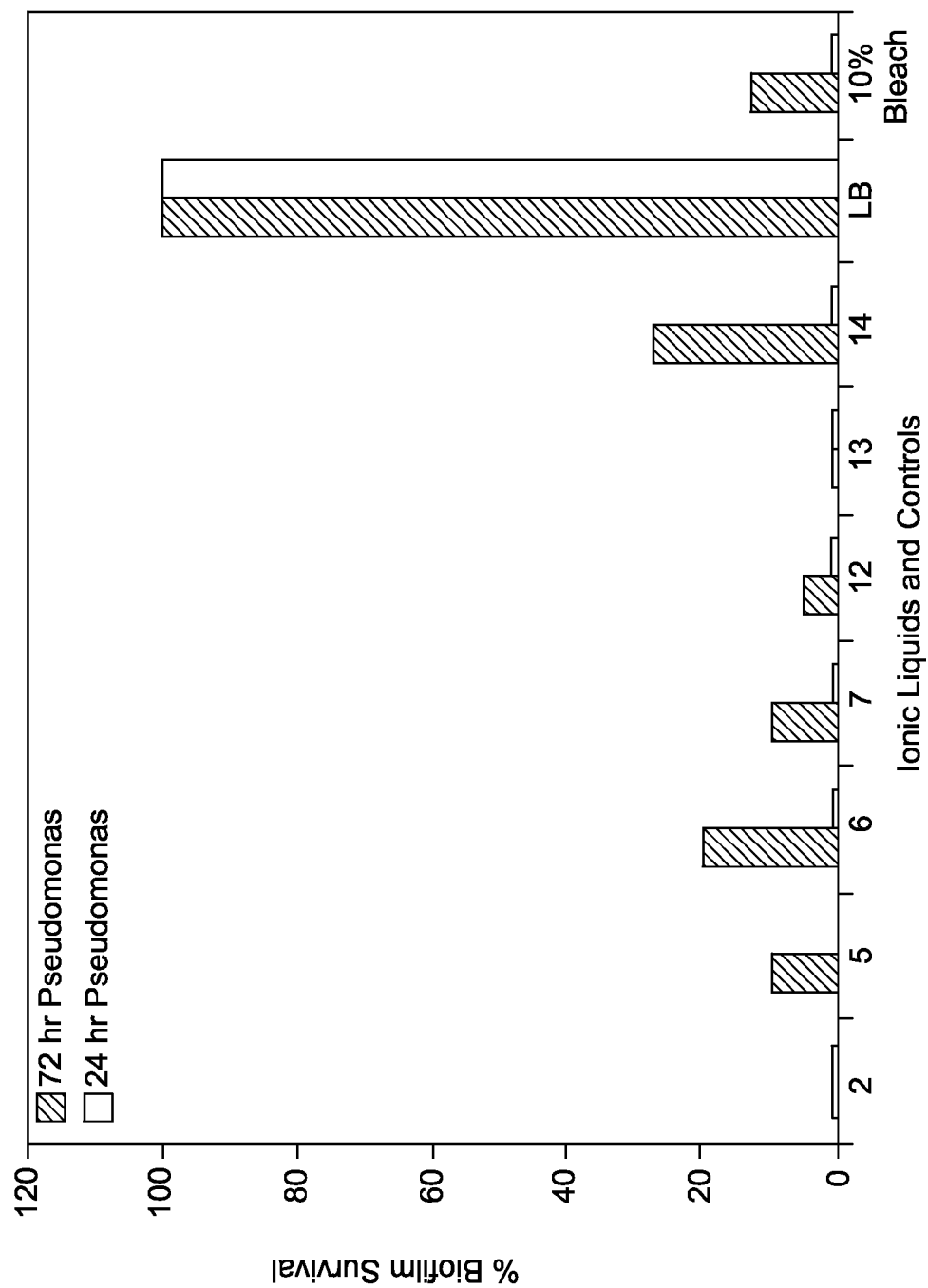
Figure 5C:
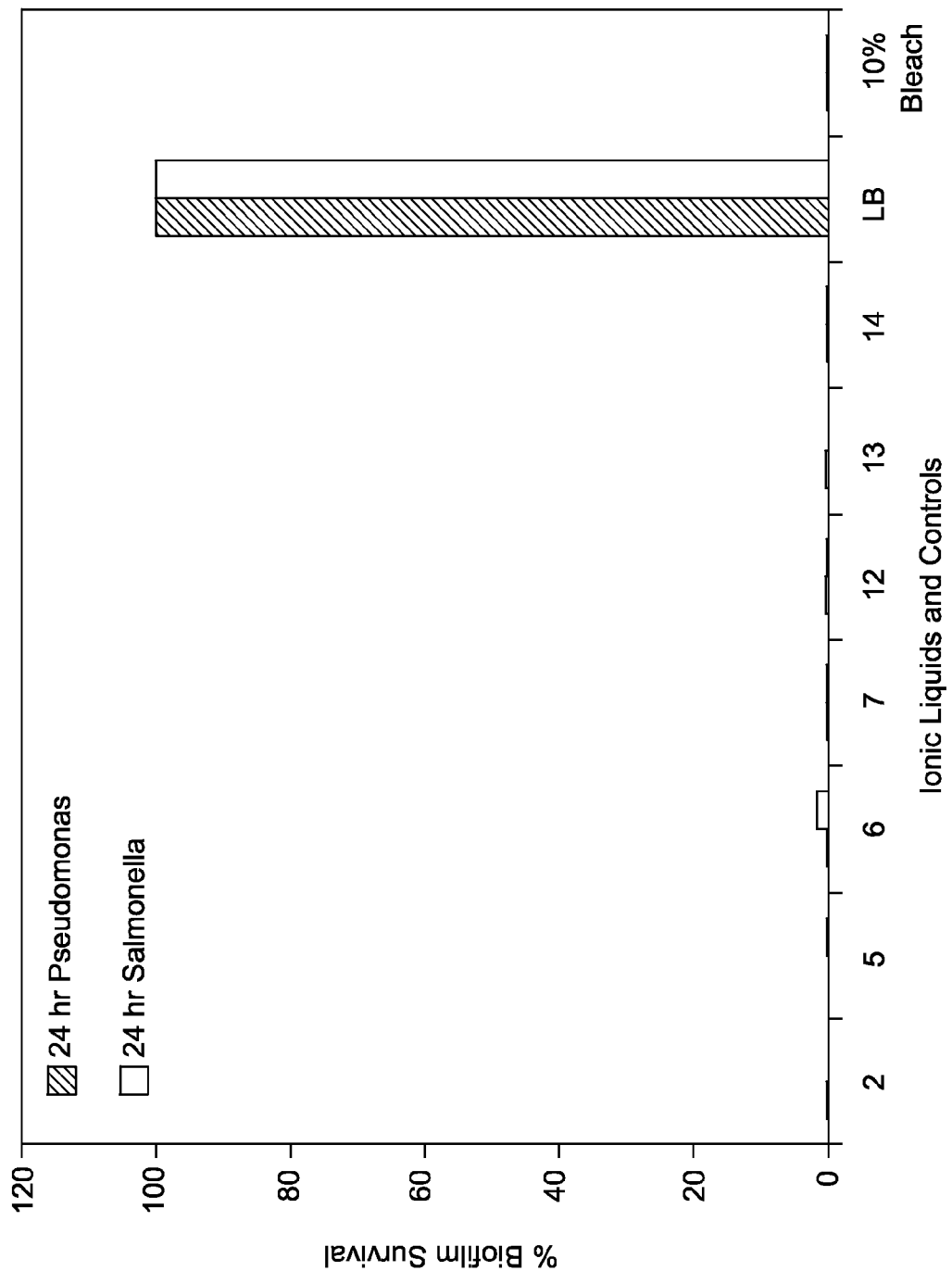

Efficacy of ILs against *pseudomonas* and *salmonella* was tested. All ILs tested showed anti-biofilm activity although at varying degrees. 72 hr films were more resistant to disruption/killing by ILs (except IL2) and controls. FIGS. 4 and 5. Several ILs are more effective against biofilms than 10% bleach. FIG. 4B. Species specific differential IL efficacy may exist. This can be seen in the plots of *Pseudomonas* vs. *Salmonella*. See FIG. 4C. Data suggests that ionic liquids have the potential to disrupt bacterial biofilm EPS and kill pathogenic bacteria. See FIGS. 4 and 5.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A deep eutectic solvent,
   wherein the deep eutectic solvent consists of a cationic component and an anionic component,
   wherein the anionic component is selected from the group consisting of bistriflimide, geranate, oleate, hexanoate, dodecyldimethyl ammonia propane sulfonate, N-Lauryl sarcosinate, and geraniolate,
   wherein the cationic component is selected from the group consisting of benzyl pyridinium, benzyl dimethyl dodecyl ammonium a choline cation, phosphonium, tetraalkylphosphonium, and benzethonium, and
   wherein the deep eutectic solvent has a melting point lower than the melting points of the cationic component and anionic component individually.

2. The deep eutectic solvent of claim 1, wherein at least one of the anionic component and cationic component is irritating to the skin when applied in the absence of the other component.

3. The deep eutectic solvent of claim 1, wherein the anionic component is geranate.

4. The deep eutectic solvent of claim 1, wherein the cationic component is a choline cation and wherein the anionic component is geranate.

5. The deep eutectic solvent of claim 1, wherein the cationic component and the anionic component are in a molar ratio ranging from 1:1 to 1:2 (cationic component to anionic component).

6. The deep eutectic solvent of claim 1, wherein the deep eutectic solvent is choline geranate.

7. The deep eutectic solvent of claim 4, wherein the cationic component and the anionic component are in a molar ratio ranging from 1:1 to 1:2 (cationic component to anionic component).

* * * * *